(12) United States Patent
Shinde et al.

(10) Patent No.: US 11,751,572 B2
(45) Date of Patent: Sep. 12, 2023

(54) MICROALGAE-BASED COMPOSITIONS FOR BENEFITING PLANTS AND METHODS OF APPLICATION

(71) Applicant: HELIAE DEVELOPMENT, LLC, Gilbert, AZ (US)

(72) Inventors: Sandip Shinde, Gilbert, AZ (US); Manikandadas Mathilakathu Madathil, Gilbert, AZ (US); Laura Carney, Chandler, AZ (US)

(73) Assignee: HELIAE DEVELOPMENT, LLC, Gilbert, AZ (US)

( * ) Notice: Subject to any disclaimer, the term of this patent is extended or adjusted under 35 U.S.C. 154(b) by 37 days.

(21) Appl. No.: 17/379,979

(22) Filed: Jul. 19, 2021

(65) Prior Publication Data
US 2021/0337805 A1 Nov. 4, 2021

Related U.S. Application Data

(63) Continuation of application No. 16/333,594, filed as application No. PCT/US2017/051678 on Sep. 15, 2017, now Pat. No. 11,109,595.

(60) Provisional application No. 62/462,654, filed on Feb. 23, 2017, provisional application No. 62/462,608, filed on Feb. 23, 2017, provisional application No. 62/462,619, filed on Feb. 23, 2017, provisional application No. 62/462,684, filed on Feb. 23, 2017, provisional application No. 62/462,642, filed on Feb. 23, 2017, provisional application No. 62/410,980, filed on Oct. 21, 2016, provisional application No. 62/410,931, filed on Oct. 21, 2016, provisional application No. 62/410,949, filed on Oct. 21, 2016, provisional application No. 62/410,968, filed on Oct. 21, 2016, provisional application No. 62/411,131, filed on Oct. 21, 2016, provisional application No. 62/410,942, filed on Oct. 21, 2016, provisional application No. 62/411,151, filed on Oct. 21, 2016, provisional application No. 62/410,957, filed on Oct. 21, 2016, provisional application No. 62/395,069, filed on Sep. 15, 2016, provisional application No. 62/395,070, filed on Sep. 15, 2016, provisional application No. 62/395,061, filed on Sep. 15, 2016, provisional application No. 62/395,181, filed on Sep. 15, 2016, provisional application No. 62/395,072, filed on Sep. 15, 2016, provisional application No. 62/395,051, filed on Sep. 15, 2016, provisional application No. 62/395,066, filed on Sep. 15, 2016, provisional application No. 62/395,182, filed on Sep. 15, 2016, provisional application No. 62/395,178, filed on Sep. 15, 2016.

(30) Foreign Application Priority Data

Jun. 16, 2017 (WO) ............... PCT/US2017/037878
Jun. 16, 2017 (WO) ............... PCT/US2017/037880

(51) Int. Cl.
| | | |
|---|---|---|
| A01N 63/00 | (2020.01) | |
| A01N 65/03 | (2009.01) | |
| A61P 31/00 | (2006.01) | |
| A61P 31/10 | (2006.01) | |
| A61K 35/02 | (2015.01) | |

(52) U.S. Cl.
CPC .................................. *A01N 63/00* (2013.01)

(58) Field of Classification Search
None
See application file for complete search history.

(56) References Cited

U.S. PATENT DOCUMENTS

| | | | | |
|---|---|---|---|---|
| 9,386,774 | B2 * | 7/2016 | Shinde | ............... A01N 65/03 |
| 10,357,038 | B2 * | 7/2019 | Shinde | ............... A01N 63/00 |
| 10,517,303 | B2 * | 12/2019 | Shinde | ............... C12N 1/12 |
| 10,631,543 | B2 * | 4/2020 | Carney | ............... A01N 63/20 |
| 10,645,937 | B2 * | 5/2020 | Carney | ............... A01N 65/03 |
| 10,694,751 | B2 * | 6/2020 | Carney | ............... A01N 63/30 |
| 10,701,941 | B2 * | 7/2020 | Carney | ............... C05F 11/08 |
| 11,039,622 | B2 * | 6/2021 | Shinde | ............... A01N 65/03 |
| 11,109,595 | B2 * | 9/2021 | Shinde | ............... A61P 31/10 |
| 11,197,474 | B2 * | 12/2021 | Shinde | ............... A01H 5/10 |
| 11,259,527 | B2 * | 3/2022 | Shinde | ............... C05F 11/08 |
| 2014/0090431 | A1 * | 4/2014 | Blotsky | ............... C05F 11/08 |
| | | | | 510/109 |
| 2014/0298717 | A1 * | 10/2014 | Ayers | ............... C12M 37/00 |
| | | | | 47/1.4 |

FOREIGN PATENT DOCUMENTS

| | | | | |
|---|---|---|---|---|
| JP | 60069183 | A * | 4/1985 | |
| JP | 2006083360 | A * | 3/2006 | ............ B82Y 30/00 |
| RU | 2562544 | C2 * | 9/2015 | |

OTHER PUBLICATIONS

Watkinson et al.( Efficacy of non-chemical weed control during plug establishment of a wildflower meadow(Journal of Environmental Horticulture, (Jun. 2007) vol. 25, No. 2, pp. 83-88). (Year: 2007).*

* cited by examiner

*Primary Examiner* — Alton N Pryor
(74) *Attorney, Agent, or Firm* — Timothy Marc Shropshire

(57) ABSTRACT

The present disclosure provides a method of increasing aggregation in a soil comprising the step of administering to the soil an amount of a microalgae material to increase aggregation in the soil compared to a substantially identical untreated soil, wherein the microalgae material comprises *Chlorella* cells and/or *Schizochytrium* cells. Also disclosed is a method of enhancing the active carbon score of a soil, comprising administering an amount of a microalgae material to the soil to increase the active carbon score of the soil compared to a substantially identical untreated soil, wherein the microalgae material comprises *Chlorella* cells and/or *Schizochytrium* cells.

20 Claims, 14 Drawing Sheets

MICROALGAE-BASED COMPOSITIONS FOR BENEFITING PLANTS AND METHODS OF APPLICATION

CROSS REFERENCE TO RELATED APPLICATIONS

The present application is a Continuation patent application of U.S. patent application Ser. No. 16/333,594, filed Mar. 14, 2019 (published as US20200060283), entitled Microalgae Based Compositions for Benefiting Plants and Methods of Application, which is the U.S. National Stage of International Application No. PCT/US2017/051678, filed Sep. 15, 2017, entitled Microalgae-Based Compositions for Benefiting Plants and Methods of Application, which claims the benefit of and priority to U.S. Provisional Application No. 62/395,178, filed Sep. 15, 2016, entitled Microalgae Based Composition for Benefiting Plants and Methods of Application; U.S. Provisional Application No. 62/410,931, filed Oct. 21, 2016, entitled Microalgae Based Compositions for Benefiting Plants and Methods of Application; U.S. Provisional Application No. 62/462,654, filed Feb. 23, 2017, entitled Microalgae Based Compositions for Benefiting Plants and Methods of Application; U.S. Provisional Application No. 62/395,051, filed Sep. 15, 2016, entitled Extracted *Chlorella* Oil and Biomass Compositions for Plants and Methods of Application; U.S. Provisional Application No. 62/462,684, filed Feb. 23, 2017, entitled Extracted *Chlorella* Oil and Biomass Compositions for Plants and Methods of Application; U.S. Provisional Application No. 62/395,061 filed Sep. 15, 2016, entitled *Galdieria* Based Compositions for Plants and Methods of Application; U.S. Provisional Application No. 62/395,066 filed Sep. 15, 2016, entitled *Haematococcus* Whole Biomass and Extracted Oil Based Compositions for Plants and Methods of Applications; U.S. Provisional Application No. 62/395,069, filed Sep. 15, 2016, entitled *Isochrysis* Based Compositions for Plants and Methods of Application; U.S. Provisional Application No. 62/410,942 filed Oct. 21, 2016, entitled *Isochrysis* Based Composition for Plants and Methods of Application; U.S. Provisional Application No. 62/462,619, filed Feb. 23, 2017, entitled *Isochrysis* Based Compositions for Plants and Methods of Application; U.S. Provisional Application No. 62/395,181, filed Sep. 15, 2016, entitled *Nannochloropsis* Based Compositions for Plants and Methods of Application; U.S. Provisional Application No. 62/410,949, filed Oct. 21, 2016, entitled *Nannochloropsis* Based Compositions for Plants and Methods of Application; U.S. Provisional Patent Application No. 62/395,182, filed Sep. 15, 2016, entitled *Porphyridium* Based Compositions for Plants and Methods of Application; U.S. Provisional Patent Application No. 62/410,957, filed Oct. 21, 2016, entitled *Porphyridium* Based Compositions for Plants and Methods of Application; U.S. Provisional Patent Application No. 62/395,070, filed Sep. 15, 2016, entitled *Schizochytrium* Based Compositions for Plants and Methods of Application; U.S. Provisional Patent Application No. 62/410,968, filed Oct. 21, 2016, entitled *Schizochytrium* Based Compositions for Plants and Methods of Application; U.S. Provisional Patent Application No. 62/462,642, filed Feb. 23, 2017, entitled *Schizochytrium* Based Compositions for Plants and Methods of Application; U.S. Provisional Patent Application No. 62/395,072 filed Sep. 15, 2016, entitled *Tetraselmis* Based Compositions for Plants and Methods of Application; U.S. Provisional Patent Application No. 62/410,980 filed Oct. 21, 2016, entitled Pavlova Based Compositions for Benefiting Plants and Methods of Application; U.S. Provisional Patent Application No. 62/411,131, filed Oct. 21, 2016, entitled *Spirulina* Based Compositions for Benefiting Plants and Methods of Application; U.S. Patent Application No. 62/462,608, filed Feb. 23, 2017, entitled *Scenedesmus* Based Compositions for Benefiting Plants and Methods of Application and U.S. Patent Application No. 62/411,151, filed Oct. 21, 2016, entitled *Scenedesmus* Based Compositions for Benefiting Plants and Methods of Application; International Application No. PCT/US2017/051678 claims the benefit of International Patent Application Nos. PCT/US2017/037878, filed Jun. 16, 2017, entitled Microalgae-Based Composition, and Methods of its Preparation and Application to Plants and PCT/US2017/037880, filed Jun. 16, 2017, entitled Microalgae-Based Compositions for Benefiting Plants and Methods of Application. The entire contents of all of the foregoing applications are hereby incorporated by reference herein.

BACKGROUND

Seed emergence occurs as an immature plant breaks out of its seed coat, typically followed by the rising of a stem out of the soil. The first leaves that appear on many seedlings are the so-called seed leaves, or cotyledons, which often bear little resemblance to the later leaves. Shortly after the first true leaves, which are more or less typical of the plant, appear, the cotyledons will drop off Germination of seeds is a complex physiological process triggered by imbibition of water after possible dormancy mechanisms have been released by appropriate triggers. Under favorable conditions rapid expansion growth of the embryo culminates in rupture of the covering layers and emergence of the radicle. A number of agents have been proposed as modulators of seed emergence. Temperature and moisture modulation are common methods of affecting seed emergence. Addition of nutrients to the soil has also been proposed to promote emergence of seeds of certain plants.

Additionally, whether at a commercial or home garden scale, growers are constantly striving to optimize the yield and quality of a crop to ensure a high return on the investment made in every growing season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has been proposed to promote yield and quality in certain plants. The effectiveness can be attributable to the ingredients or the method of preparing the product. Increasing the effectiveness of a product can reduce the amount of the product needed and increase efficiency of the agricultural process. Therefore, there is a need in the art for methods of enhancing the yield and quality of plants and plant-associated soils.

SUMMARY

Compositions and methods are described herein improving at least one plant and/or soil characteristic. The compositions can include cells (i.e., biomass) or extracts from the microalgae in various states, such as but not limited to, cells with reduced protein content, whole cells, lysed cells, dried cells, excreted products (e.g., excreted polysaccharides [EPS]), extracted oil, extracted protein, cells that have been subjected to an oil or protein extraction process, and combinations thereof. In this respect, an "extract0' in the context of the invention can mean biomass that has been subjected to extraction of one or more fractions, such as one or more lipid fractions and/or it can mean a lipid fraction, a protein faction, or other fraction that has been extracted from "whole" biomass/cells. The composition can include microalgae derived products as the primary or sole active ingredient, or in combination with other active ingredients such as, but not limited to, extracts or biomass from macroalgae (e.g., kelp such as *Ascophyllum nodosum*, *Kappaphycus alvarezii*, or one or more extracts thereof). The compositions can be in the form of a liquid or dry form (powder, or the like). The compositions can be stabilized through the addition of stabilizers suitable for plants, pasteurization, and combinations thereof. The methods can include applying the compositions to plants or seeds in a variety of methods, such as but not limited to, soil application, foliar application, seed treatments (such as seed coating), and/or hydroponic application. The methods can include single or multiple applications of the compositions, and can also include low concentrations of microalgae cells (i.e., biomass), excreted products, or extracts.

In one non-limiting embodiment, a method of plant enhancement can include administering to a plant, seedling, or seed a composition treatment comprising 0.001-0.1% by weight of microalgae biomass to enhance at least one plant characteristic, which in some embodiments is whole microalgae biomass. "Whole microalgae biomass" means a composition wherein substantially all of the components of the microalgae cells produced in the composition during culturing/growth remain present (e.g., in certain aspects of the invention at least about 90 "o of the cellular components, at least about 95% of the cellular components, or at least about 99% of the cellular components produced during growth/culturing remain present). This kind of composition ("whole microalgae biomass") is distinct from, for example, a composition formed from an extract taken from a microalgae composition, which might be composed primarily or entirely of one or more microalgae-derived oils or proteins.

"Microalgae biomass" means any composition wherein a majority of the cellular components of the whole microalgae biomass are maintained in the composition (by number of components, but not necessarily by weight). Thus, for example, a collection of microalgae cells that is subjected to an oil extraction would be considered microalgae biomass, but not be considered whole microalgae biomass. A microalgae biomass subjected to processing to remove one or more of its cellular components also may be referred to as a "post-extraction microalgae biomass".

In some embodiments, the composition can be applied when the plant is under at least one of salt stress and temperature stress conditions. In some embodiments, the microalgae biomass can have been subjected to a protein extraction process. In some embodiments, the microalgae biomass can have been subjected to an oil extraction process. In some embodiments, the microalgae can include at least one from the group consisting of *Botryococcus*, *Scenedesmus*, *Pavlova*, *Phaeodactylum*, *Nannochloropsis*, *Spirulina*, *Galdieria*, *Haematococcus*, *Isochrysis*, *Porphyridium*, *Schizochytrium*, and *Tetraselmis*.

In another non-limiting embodiment, a composition can include microalgae biomass, in a concentration in the range of 0.001-0.1% by weight. For sake of illustration, a composition can have a microalgae biomass concentration within a narrower range of concentrations such as 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%>, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In another non-limiting embodiment, a method of preparing a composition can include diluting the concentration of microalgae biomass to a concentration in the range of 0.001-0.1<% by weight or that is within the range 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In another non-limiting embodiment, a method of preparing a composition can include: subjecting microalgae cells to an oil extraction process; separating the extracted oil from the extracted biomass; and diluting the concentration of extracted biomass to a concentration in the range of 0.001-0.1% by weight or that is in a range such as 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003°/o, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In one non-limiting embodiment, a method of plant enhancement can include administering to a plant, seedling, or seed a composition treatment comprising 0.0001-0.01% by weight of extracted microalgae oil (or in one of the narrower ranges described above, such as 0.001-0.01%, 0.005-0.01%, 0.0075-0.01%, or 0.009-0.01%) to enhance at least one plant characteristic. In some embodiments, the composition can be applied when the plant is under at least one of salt stress and temperature stress conditions. In some embodiments, the microalgae cells can have a low protein content. In some embodiments, the microalgae can include at least one from the group consisting of *Botryococcus*, *Scenedesmus*, *Pavlova*, *Phaeodactylum*, *Spirulina*, *Galdieria*, *Chlorella*, *Haematococcus*, *Isochrysis*, *Nannochloropsis*, *Porphyridium*, *Schizochytrium*, and *Tetraselmis*.

In another non-limiting embodiment, a composition can include extracted microalgae oil, in a concentration in the range of 0.0001-0.01% by weight (or one of the other ranges described above).

In another non-limiting embodiment, a method of preparing a composition can include: subjecting microalgae cells to an oil extraction process; separating the extracted oil from the extracted biomass; and diluting the concentration of extracted oil to a concentration in the range of 0.0001-0.01% by weight (or one of the narrower ranges described above).

In one non-limiting embodiment, a method of plant enhancement can include administering to a plant, seedling, or seed, or to soil associated with the plant (or another medium associated with the plant, such as a hydroponic medium), a composition treatment comprising 0.001-0.1% by weight of extracted microalgae protein from at least one from the group consisting of *Galdieria*, *Porphyridium*, and *Spirulina*.to enhance at least one plant characteristic. In some embodiments, the composition can be applied when the plant is under at least one of salt stress and temperature stress conditions.

In another non-limiting embodiment, a composition can include extracted microalgae protein, in a concentration in the range of 0.001-0.1% by weight or in one of the narrower ranges provided above such as 0.002%-0.090% such as 0.003%-0.085%, 0.004%-0.08%>, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%.

In another non-limiting embodiment, a method of preparing a composition can include: subjecting microalgae cells to a protein extraction process; separating the extracted protein fraction; and diluting the concentration of extracted protein fraction to a concentration in the range of 0.001-0.1% by weight or one of the narrower ranges provided above.

In one non-limiting embodiment, a method of plant enhancement can include administering to a plant, seedling, or seed a composition treatment comprising 0.001-0.1% by weight of EPS from *Porphyridium* (or a concentration such as 0.002%-0.09%, such as 0.003%-0.085%, 0.004%-0.08%, 0.005%-0.075%, 0.0075%-0.075%, 0.008%-0.08%, 0.009%-0.09%, 0.01%-0.1%, 0.015%-0.09%, 0.02%-0.08%, 0.025%-0.075%, or any similar amount within these ranges such as a range with a lower end of 0.001%, 0.003%, 0.005%, 0.007%, 0.009%, 0.01%, 0.02%, 0.03%, 0.04%, or 0.05% and an upper end of the range of 0.1%, 0.09%, 0.085%, 0.08%, 0.075%, 0.07%, or 0.05%) to enhance at least one plant and/or soil characteristic. In some embodiments, the composition can be applied when the plant is under at least one of salt stress and temperature stress conditions.

In another non-limiting embodiment, a composition can include EPS from *Porphyridium*, in a concentration in the range of 0.001-0.1% by weight or one of the narrower ranges described elsewhere herein.

In another non-limiting embodiment, a method of preparing a composition can include: isolating EPS from a culture of *Porphyridium*; and diluting the concentration of isolated EPS to a concentration in one of the disclosed ranges provided herein, such as in the range of 0.001-0.1% by weight.

In another non-limiting embodiment, a method of plant enhancement can include administering to a plant, seedling, or a seed a composition treatment comprising 10% by weight of microalgae biomass to soil at an application rate in the range of 0.5-20 liters per acre to enhance at least one plant and/or soil characteristic. In an exemplary embodiment, the application rate can be in the range of 3.7 to 15 liters per acre. In some embodiments, the microalgae can comprise at least one microalgae from the group consisting of *Aurantiochytrium, Spirulina, Isochrysis*, and *Scenedesmus*.

DETAILED DESCRIPTION

Figure 1:
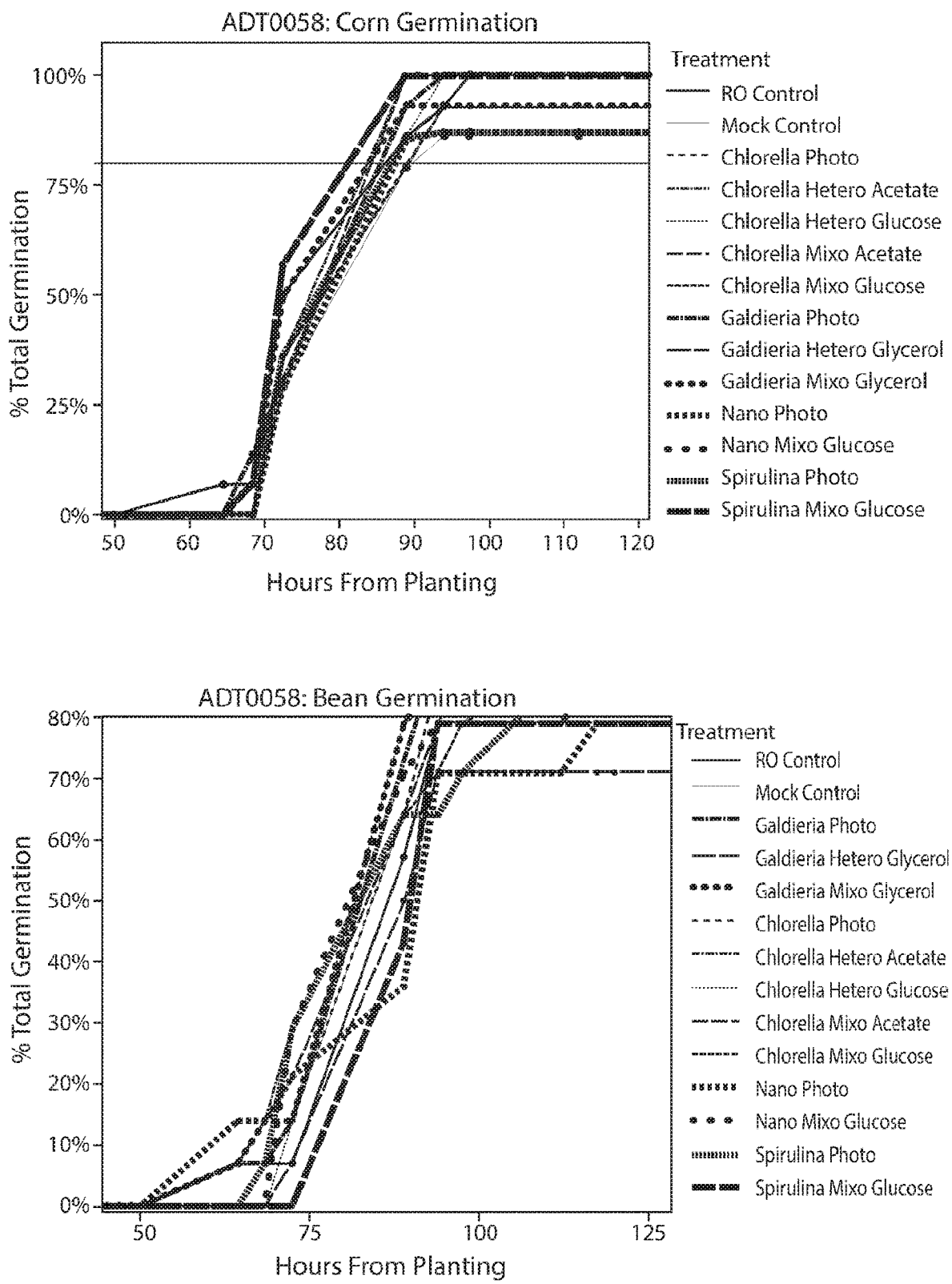
FIG. 1 depicts results of experiments involving microalgae-based compositions on corn, bean and pepper seed germination.
Figure 1:
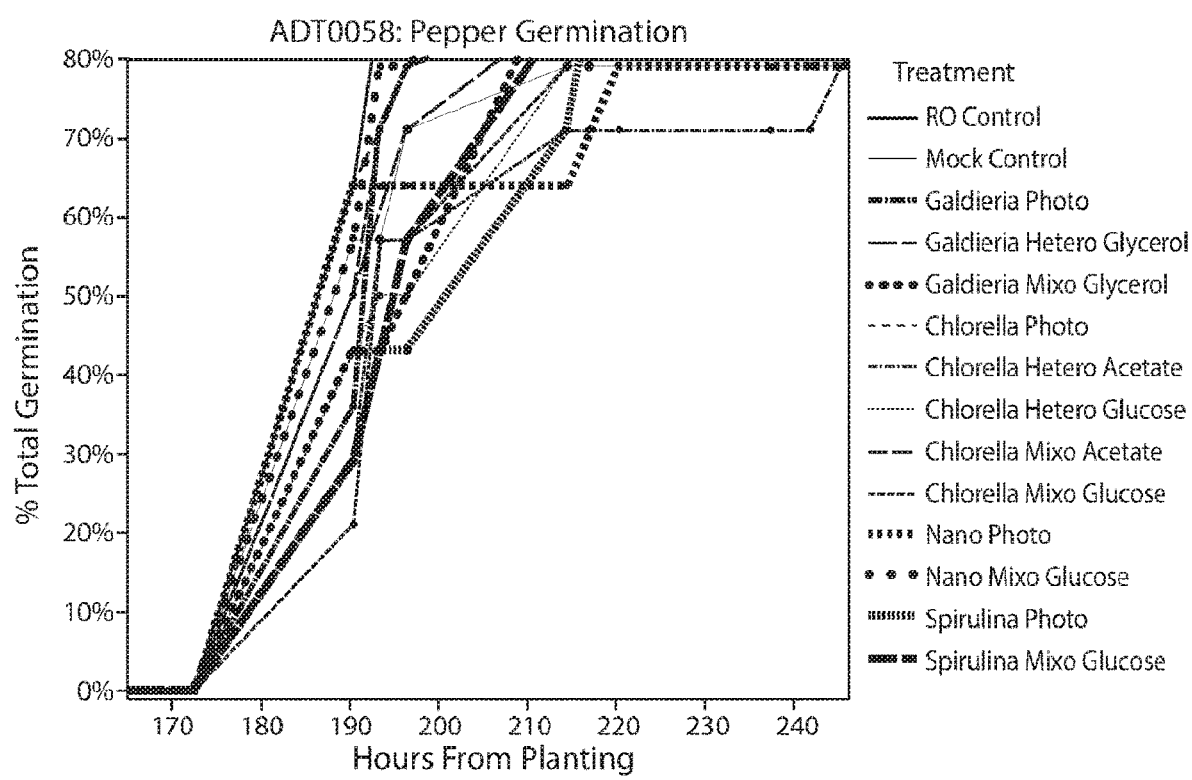
Figure 2:
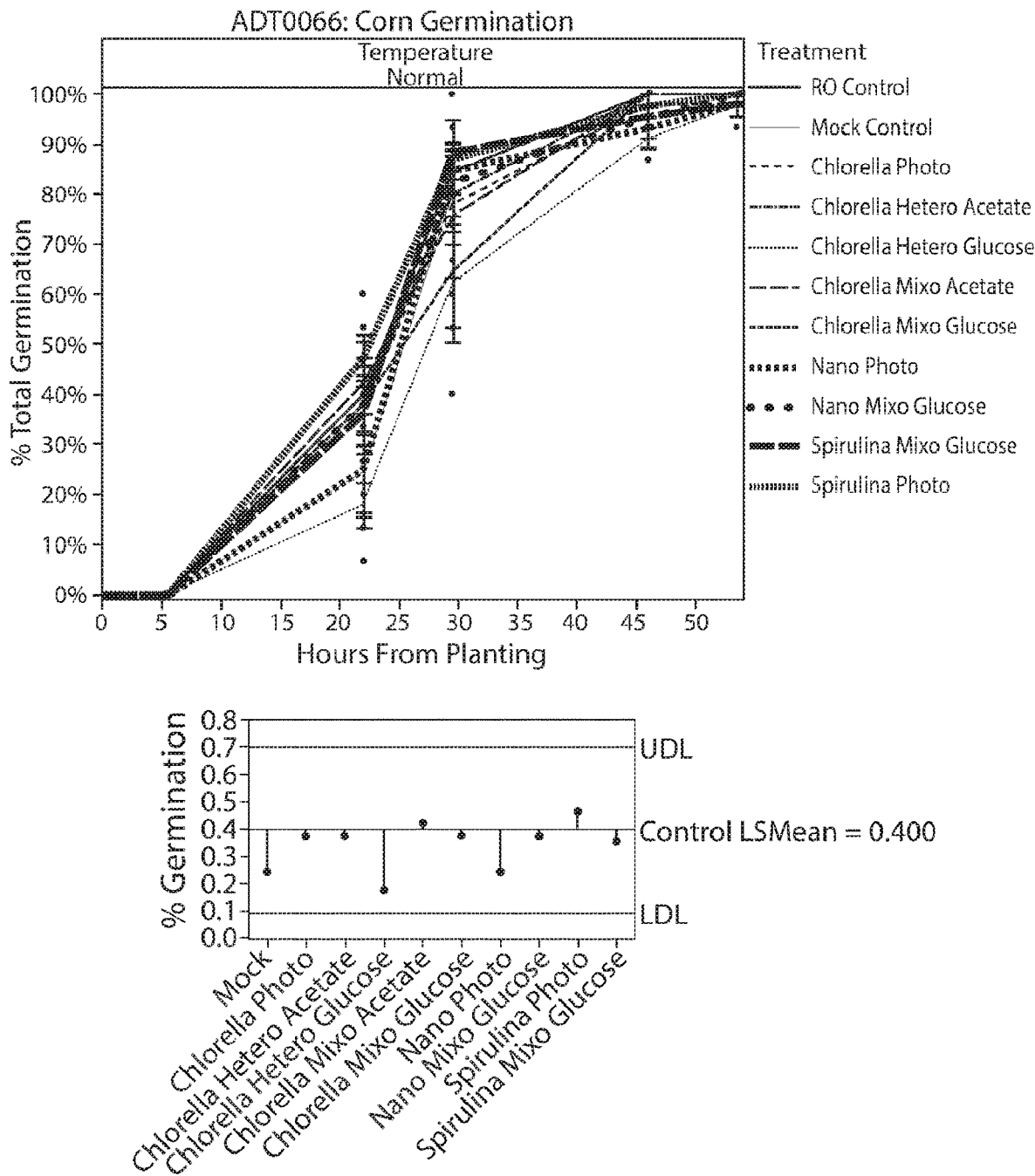
FIG. 2 depicts results of experiments involving microalgae-based compositions on corn, bean and pepper seed germination.
Figure 2:
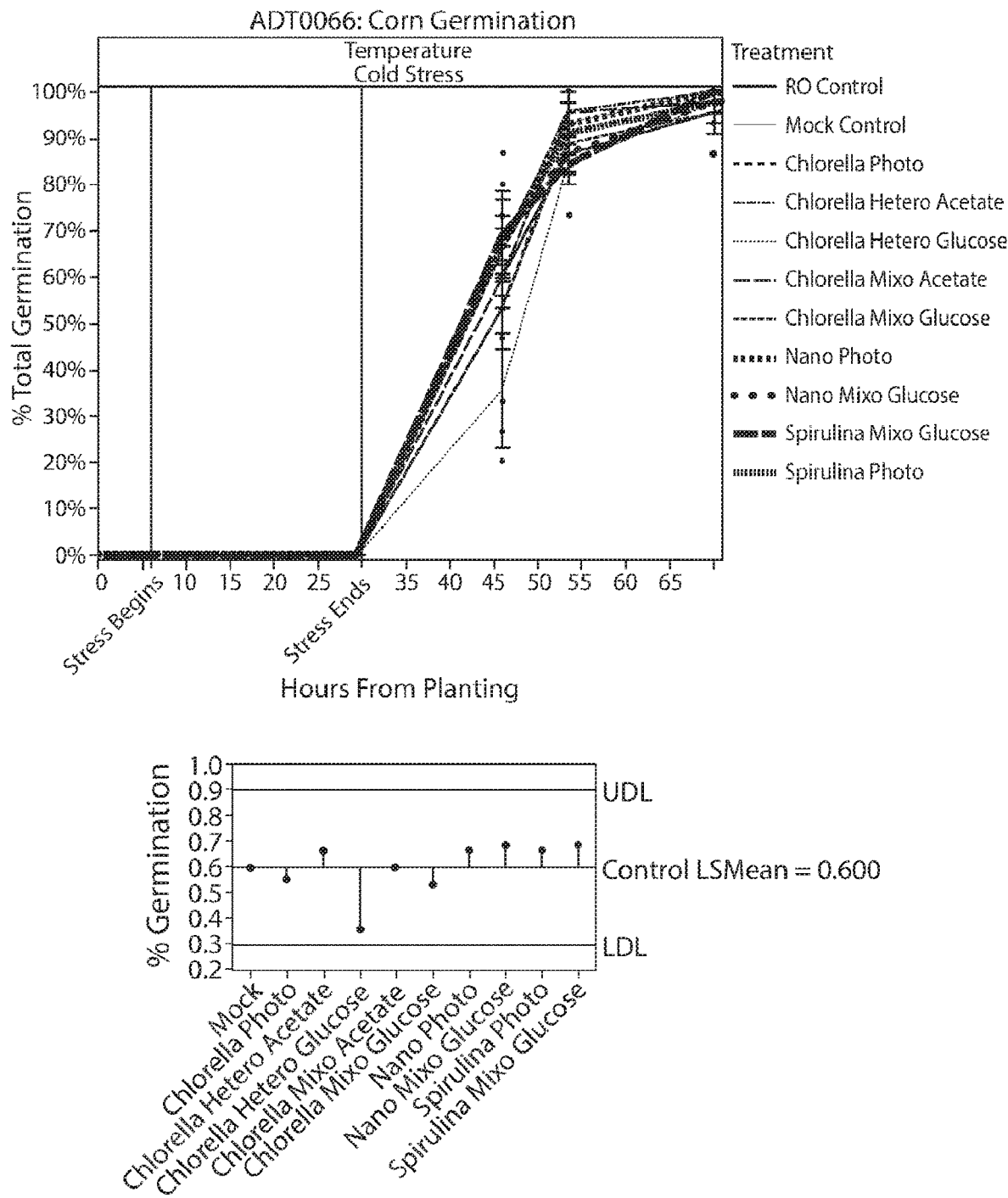
Figure 2:
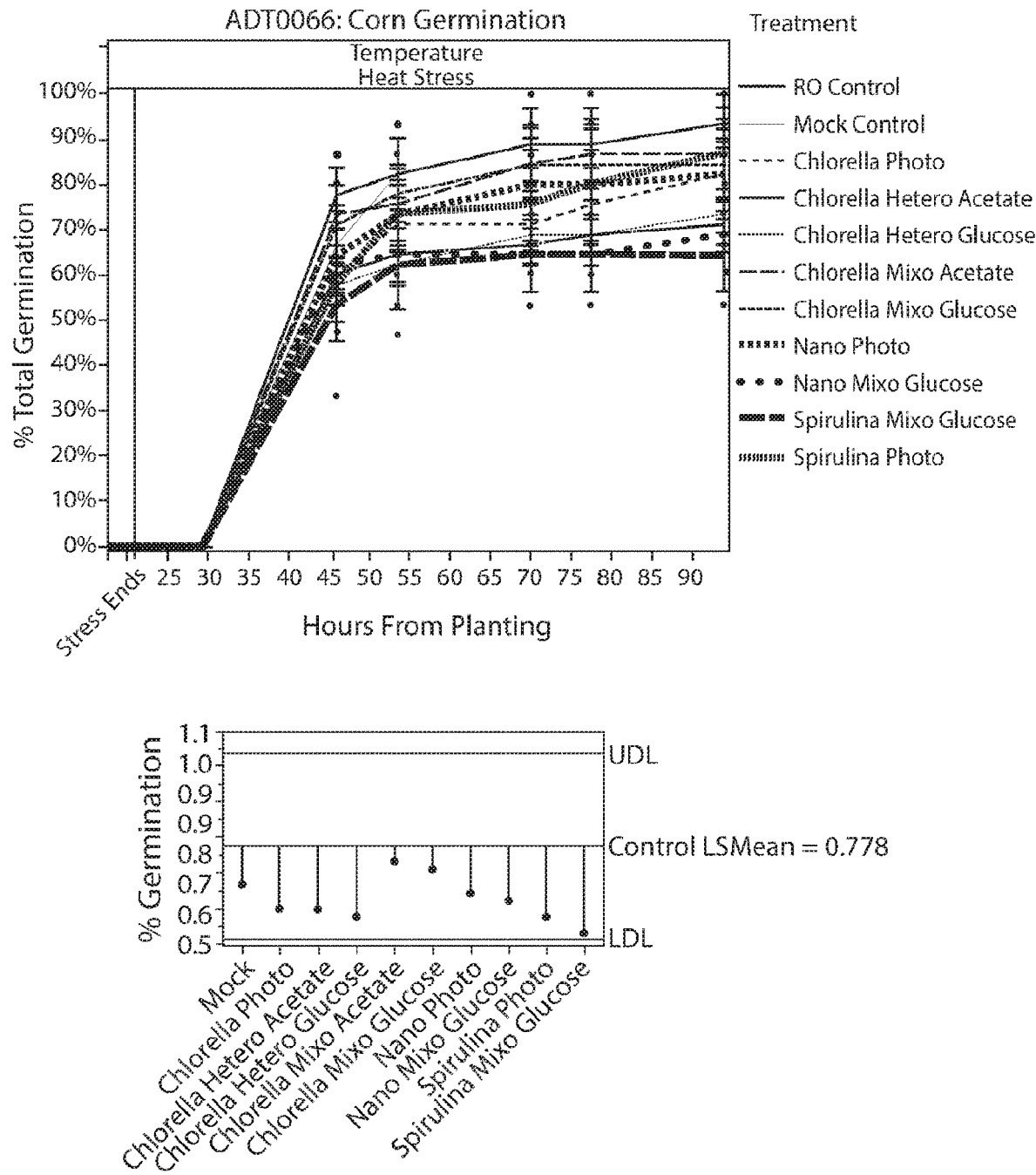
Figure 3:
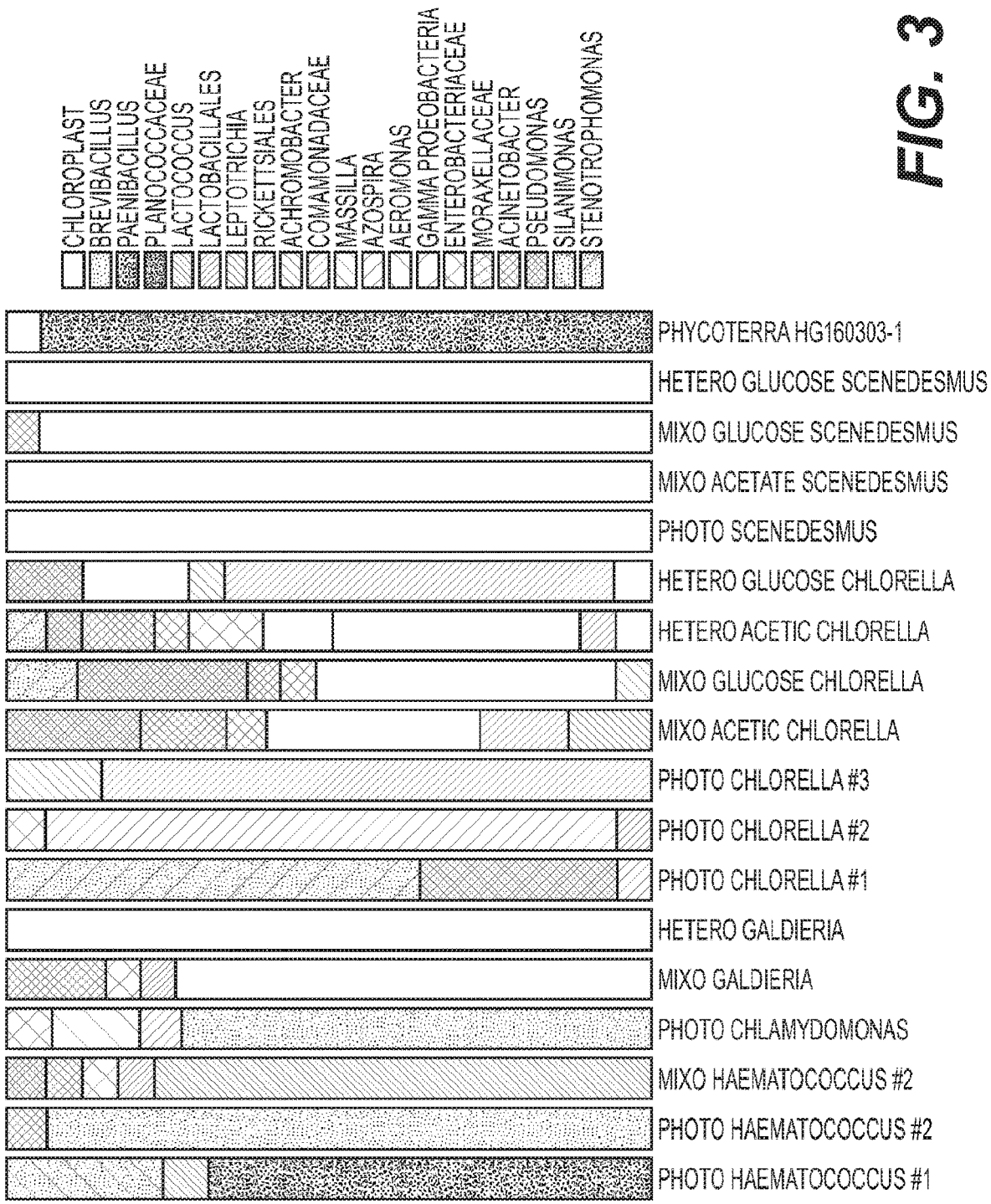
FIG. 3 depicts a composition analyses of example microalgae-based compositions.

Many plants can benefit from the application of liquid compositions that provide a bio-stimulatory effect. Non-limiting examples of plant families that can benefit from such compositions include plants from the following: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Laurasia, Piperaceae, and Proteaceae. A biostimulatory effect can mean an effect that results directly in promotion of plant growth, plant quality, plant health, plant pest and/or disease resistance, plant productivity, and/or plant longevity, or that results in the promotion of organisms in the plant microbiome, such as beneficial bacteria in the soil, either directly or through improving one or more physical characteristics of the soil. A biostimulatory effect can arise from the direct administration of products to plants, such as by foliar application to leaves, or indirectly through administration of products to soil to improve the environment of the plant (thereby indirectly providing benefits to the plant) and/or to result in uptake of the composition or elements of the composition by the plants to promote one or more detectable, desirable and/or beneficial biological effects/results.

The Solanaceae plant family includes a large number of agricultural crops, medicinal plants, spices, and ornamentals in it's over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding *Antarctica*, and thus have a widespread importance in agriculture across the globe.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding *Antarctica*, and thus have a widespread importance in agriculture across the globe. Besides food, plants in the Fabaceae family can be used to produce natural gums, dyes, and ornamentals.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgrn, 419 tifway, tif sport).

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important in the production of fruit from plants is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem.

Also important in the production of fruit from plants is the yield and quality of fruit, which can be quantified as the number, weight, color, firmness, ripeness, moisture, degree of insect infestation, degree of disease or rot, and degree of sunburn of the fruit. A method of treating a plant to directly improve the characteristics of the plant, or to indirectly enhance the chlorophyll level of the plant for photosynthetic capabilities and health of the plant's leaves, roots, and shoot to enable robust production of fruit is therefore valuable in increasing the efficiency of marketable production. Marketable and unmarketable designations can apply to both the plant and fruit, and can be defined differently based on the end use of the product, such as but not limited to, fresh market produce and processing for inclusion as an ingredient in a composition. The marketable determination can assess such qualities as, but not limited to, color, insect damage, blossom end rot, softness, and sunburn. The term total production can incorporate both marketable and unmarketable plants and fruit. The ratio of marketable plants or fruit to unmarketable plants or fruit can be referred to as utilization and expressed as a percentage. The utilization can be used as an indicator of the efficiency of the agricultural process as it shows the successful production of marketable plants or fruit, which will be obtain the highest financial return for the grower, whereas total production will not provide such an indication.

To achieve such improvements in emergence, maturation, and yield of plants, a method to treat such seeds and plants, and soil, a low concentration microalgae based composition, in a dried or liquid solution form, was developed. Microalgae can be grown in heterotrophic, mixotrophic, and phototrophic conditions. Culturing microalgae in heterotrophic conditions comprises supplying organic carbon (e.g., acetic acid, acetate, glucose) to cells in an aqueous culture medium comprising trace metals and nutrients (e.g., nitrogen, phosphorus). Culturing microalgae in mixotrophic conditions comprises supplying light and organic carbon (e.g., acetic acid, acetate, glucose) to cells in an aqueous culture medium comprising trace metals and nutrients (e.g., nitrogen, phosphorus). Culturing microalgae in phototrophic conditions comprises supplying light and inorganic carbon (e.g., carbon dioxide) to cells in an aqueous culture medium comprising trace metals and nutrients (e.g., nitrogen, phosphorus).

In some embodiments, the microalgae cells can be harvested from a culture and used as whole cells in a liquid composition for application to seeds and plants, while in other embodiments the harvested microalgae cells can be subjected to downstream processing and the resulting biomass or extract can be used in a dried composition (e.g., powder, pellet) or a liquid composition (e.g., suspension, solution) for application to plants, soil, or a combination thereof. Non-limiting examples of downstream processing comprise: drying the cells, lysing the cells, and subjecting the harvested cells to a solvent or supercritical carbon dioxide extraction process to isolate an oil or protein. In some embodiments, the extracted (i.e., residual) biomass remaining from an extraction process can be used alone or in combination with other microalgae or extracts in a liquid composition for application to plants, soil, or a combination thereof. By subjecting the microalgae to an extraction process the resulting biomass is transformed from a natural whole state to a lysed condition where the cell is missing a significant amount of the natural components, thus differentiating the extracted microalgae biomass from that which is found in nature. Excreted products from the microalgae can also be isolated from a microalgae culture using downstream processing methods.

In some embodiments, microalgae can be the dominate active ingredient source in the composition. In some embodiments, the microalgae population of the composition can include whole biomass, substantially extracted biomass, excreted products (e.g., EPS), extracted protein, or extracted oil. In some embodiments, microalgae include at least 99% of the active ingredient sources of the composition. In some embodiments, microalgae include at least 95% of the active ingredient sources of the composition. In some embodiments, microalgae include at least 90% of the active ingredient sources of the composition. In some embodiments, microalgae include at least 80% of the active ingredient sources of the composition. In some embodiments, microalgae include at least 70% of the active ingredient sources of the composition. In some embodiments, microalgae include at least 60% of the active ingredient sources of the composition. In some embodiments, microalgae include at least 50% of the active ingredient sources of the composition. In some embodiments, microalgae include at least 40% of the active ingredient sources of the composition. In some embodiments, microalgae include at least 30% of the active ingredient sources of the composition. In some embodiments, microalgae include at least 20% of the active ingredient sources of the composition. In some embodiments, microalgae include at least 10% of the active ingredient sources of the composition. In some embodiments, microalgae include at least 5% of the active ingredient sources of the composition. In some embodiments, microalgae include at least 1% of the active ingredient sources of the composition. In some embodiments, the composition lacks any detectable amount of any other active ingredient source other than microalgae. The term "substantially" herein means at least 95%, such as at least 96%, at least 97%, at least 98%, at least 99%, or more such as at least 99.2%, at least 99.5%, at least 99.75%, at least 99.8%, or at least 99.9%.

In some embodiments, microalgae biomass, excreted products, or extracts can also be mixed with biomass or extracts from other plants, microalgae, macroalgae, seaweeds, and kelp. In some embodiments, microalgae biomass, excreted products, or extracts can also be mixed with fish oil. Non-limiting examples of other plants, macroalgae, seaweeds, and kelp fractions that can be combined with microalgae cells can include species of *Lemna, Gracilaria, Kappaphycus, Ascophyllum, Macrocystis, Fucus, Laminaria, Sargassum, Turbinaria*, and *Durvilea*. In further embodiments, the extracts can comprise, but are not limited to, liquid extract from a species of *Kappaphycus*. In some embodiments, the extracts can include 50% or less by volume of the composition. In some embodiments, the extracts can include 40% or less by volume of the composition. In some embodiments, the extracts can include 30% or less by volume of the composition. In some embodiments, the extracts can include 20% or less by volume of the composition. In some embodiments, the extracts can include 10/o or less by volume of the composition. In some embodiments, the extracts can include 5/o or less by volume of the composition. In some embodiments, the extracts can include 4% or less by volume of the composition. In some embodiments, the extracts can include 3% or less by volume of the composition. In some embodiments, the extracts can include 2% or less by volume of the composition. In some embodiments, the extracts can include 1% or less by volume of the composition.

The term "microalgae" refers to microscopic single cell organisms such as microalgae, cyanobacteria, algae, diatoms, dinoflagellates, freshwater organisms, marine organisms, or other similar single cell organisms capable of growth in phototrophic, mixotrophic, or heterotrophic culture conditions.

In some embodiments, microalgae biomass, excreted product, or extracts can also be sourced from multiple types of microalgae, to make a composition that is beneficial when applied to plants or soil. Non-limiting examples of microalgae that can be used in the compositions and methods of the present invention include microalgae m the classes: Eustigmatophyceae, Chlorophyceae, Prasinophyceae, Haptophyceae, Cyanidiophyceae, Pymnesiophyceae, Porphyridiophyceae, Labyrinthulomycetes, Trebouxiophyceae, Bacillariophyceae, and Cyanophyceae. The class Lyanidiophyceae includes species of *Galdieria*. The class Chlorophyceae includes species of *Haematococcus, Scenedesmus, Chlamydomonas*, and A4cractinium. The class Prymnesiophyceae includes species of *Isochrysis* and Pavlova. The class Eustigmatophyceae includes species of *Nannochloropsis*. The class Porphyridiophyceae includes species of *Porphyridium*. The class Labyrinthulomycetes includes species of *Schizochytrium* and *Aurantiochytrium*. The class Prasinophyceae includes species of *Tetraselmis*. The class Trebouxiophyceae includes species of *Chlorella* and *Botlyococcus*. The class Bacillariophyceae includes species of *Phaeodactylum*. The class Cyanophyceae includes species of *Spirulina*.

Non-limiting examples of microalgae genus and species that can be used m the compositions and methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coife [formis* var. *tenuis, Amphora delicatissima, Amphora delicatissima* var. *capitata, Amphora* sp., *Anabaena, Ankistrodesmus, Ankistrodesmus falcatus, Aurantiochytrium* sp., *Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomonas* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella Jusca, Chlorella Jusca* var. *vacuolate, Chlorella glucotropha, Chlorella inJusionum, Chlorella inJusionum* var. *actophila, Chlorella inJusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ova/is, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* Jo. *tertia, Chlorella vulgaris* var. *autotrophica, Chlorella vulgaris* var. *viridis, Chlorella vulgaris* var. *vulgaris, Chlorella vulgaris* var. *vulgaris* Jo. *tertia, Chlorella vulgaris* var. *vulgaris* Jo. *viridis, Chlorella xanthella, Chlorella zofingiensis, Chlorella trebouxioides, Chlorella vulgaris, Chlorococcum inlusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Galdie-* ria sp., *Gleocapsa* sp., *Gloeothamnion* sp., *Haematococcus pluvialis*, *Hymenomonas* sp., *Isochrysis* a.ff *galbana*, *Isochrysis galbana*, *Lepocinclis*, *A4icractinium*, *Al onoraphidium minutum*, *Monoraphidium* sp., *Nannochloris* sp., *Nannochloropsis salina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia closterium*, *Nitzschia communis*, *Nitzschia dissipata*, *Nitzschia frustulum*, *Nitzschia hantzschiana*, *Nitzschia inconspicua*, *Nitzschia intermedia*, *Nitzschia microcephala*, *Nitzschia pusilla*, *Nitzschia pusilla elliptica*, *Nitzschia pusilla monoensis*, *Nitzschia quadrangular*, *Nitzschia* sp., *Ochromonas* sp., *Oocystis parva*, *Oocystis pusilla*, *Oocystis* sp., *Oscillatoria limnetica*, *Oscillatoria* sp., *Oscillatoria subbrevis*, *Parachlorella kessleri*, *Pascheria acidophila*, *Pavlova* sp., *Phaeodactylum tricomutum*, *Phagus*, *Phormidium*, *Platymonas* sp., *Pleurochrysis camerae*, *Pleurochrysis dentate*, *Pleurochrysis* sp., *Porphyridium* sp., *Prototheca wickerhamii*, *Prototheca stagnora*, *Prototheca portoricensis*, *Prototheca moriformis*, *Prototheca zopfii*, *Pseudochlorella aquatica*, *Pyramimonas* sp., *Pyrobotrys*, *Rhodococcus opacus*, *Sarcinoid chlysophyte*, *Scenedesmus armatus*, *Schizochytrium*, *Spirogyra*, *Spirulina platensis*, *Stichococcus* sp., *Synechococcus* sp., *Synechocystisf*, *Tagetes erecta*, *Tagetes patula*, *Tetraedron*, *Tetraselmis* sp., *Tetraselmis suecica*, *Thalassiosira weis fiogii*, and *Viridiella fridericiana*.

Analysis of the DNA sequence of the strain of *Chlorella* sp. described in the specification was done in the NCBI 18s rDNA reference database at the Culture Collection of Algae at the University of Cologne (CCAC) showed substantial similarity (i.e., greater than 95%) with multiple known strains of *Chlorella* and *Micractinium*. Those of skill in the art will recognize that *Chlorella* and *Micractinium* appear closely related in many taxonomic classification trees for microalgae, and strains and species may be re-classified from time to time. Thus, for references throughout the instant specification for *Chlorella* sp., it is recognized that microalgae strains m related taxonomic classifications with similar characteristics to the reference *Chlorella* sp. strain would reasonably be expected to produce similar results.

Additionally, taxonomic classification has also been in flux for organisms in the genus *Schizochytrium*. Some organisms previously classified as *Schizochytrium* have been reclassified as *Aurantiochytrium*, *Thraustochytrium*, or *Oblongichytrium*. See Yokoyama et al. Taxonomic rearrangement of the genus *Schizochytrium* sensu lato based on morphology, chemotaxonomic characteristics, and 18S rRNA gene phylogeny (Thrausochytriaceae, Labyrinthulomycetes): emendation for *Schizochytrium* and erection of *Aurantiochytrium* and *Oblongichytrium* gen. nov. *Mycoscience* (2007) 48:199-211. Those of skill in the art will recognize that *Schizochytrium*, *Aurantiochytrium*, *Thraustochytrium*, and *Oblongichytrium* appear closely related in many taxonomic classification trees for microalgae, and strains and species may be re-classified from time to time. Thus, for references throughout the instant specification for *Schizochytrium*, it is recognized that microalgae strains in related taxonomic classifications with similar characteristics to *Schizochytrium* would reasonably be expected to produce similar results.

By artificially controlling aspects of the microalgae culturing process such as the organic carbon feed (e.g., acetic acid, acetate), oxygen levels, pH, and light, the culturing process differs from the culturing process that microalgae experiences in nature. In addition to controlling various aspects of the culturing process, intervention by human operators or automated systems occurs during the non-axenic mixotrophic culturing of microalgae through contamination control methods to prevent the microalgae from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/O74769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus, through artificial control of aspects of the culturing process and intervening in the culturing process with contamination control methods, the microalgae culture produced as a whole and used in the described inventive compositions differs from the culture that results from a microalgae culturing process that occurs in nature.

During the mixotrophic culturing process the microalgae culture can also include cell debris and compounds excreted from the microalgae cells into the culture medium. The output of the microalgae mixotrophic culturing process provides the active ingredient for composition that is applied to plants for improving yield and quality without separate addition to or supplementation of the composition with other active ingredients not found in the mixotrophic microalgae whole cells and accompanying culture medium from the mixotrophic culturing process such as, but not limited to: microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

In some embodiments, the microalgae can be previously frozen and thawed before inclusion in the liquid composition. In some embodiments, the microalgae may not have been subjected to a previous freezing or thawing process. In some embodiments, the microalgae whole cells have not been subjected to a drying process. The cell walls of the microalgae of the composition have not been lysed or disrupted, and the microalgae cells have not been subjected to an extraction process or process that pulverizes the cells. The microalgae whole cells are not subjected to a purification process for isolating the microalgae whole cells from the accompanying constituents of the culturing process (e.g., trace nutrients, residual organic carbon, bacteria, cell debris, cell excretions), and thus the whole output from the microalgae culturing process comprising whole microalgae cells, culture medium, cell excretions, cell debris, bacteria, residual organic carbon, and trace nutrients, is used in the liquid composition for application to plants. In some embodiments, the microalgae whole cells and the accompanying constituents of the culturing process are concentrated in the composition. In some embodiments, the microalgae whole cells and the accompanying constituents of the culturing process are diluted in the composition to a low concentration. The microalgae whole cells of the composition are not fossilized. In some embodiments, the microalgae whole cells are not maintained in a viable state in the composition for continued growth after the method of using the composition in a soil or foliar application. In some embodiments, the microalgae base composition can be biologically inactive after the composition is prepared. In some embodiments, the microalgae base composition can be substantially biologically inactive after the composition is prepared. In some embodiments, the microalgae base composition can increase m biological activity after the prepared composition is exposed to air.

In some embodiments, a liquid composition can include low concentrations of bacteria contributing to the solids percentage of the composition in addition to the microalgae cells. Examples of bacteria found in non-axenic mixotrophic conditions can be found in WO2014/074769A2 (Ganuza, et al.), hereby incorporated by reference. A live bacteria count can be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture can range from $10^4$ to $10^9$ CFU/mL, and can depend on contamination control measures taken during the culturing of the microalgae. The level of bacteria in the composition can be determined by an aerobic plate count which quantifies aerobic colony forming units (CFU) in a designated volume. In some embodiments, the composition includes an aerobic plate count of 40,000-400,000 CFU/mL. In some embodiments, the composition includes an aerobic plate count of 40,000-100,000 CFU/mL. In some embodiments, the composition includes an aerobic plate count of 100,000-200,000 CFU/mL. In some embodiments, the composition includes an aerobic plate count of 200,000-300,000 CFU/mL. In some embodiments, the composition includes an aerobic plate count of 300,000-400,000 CFU/mL.

In some embodiments, the microalgae based composition can be supplemented with a supplemental nutrient such as nitrogen, phosphorus, or potassium to increase the levels within the composition to at least 1% of the total composition (i.e., addition of N, P, or K to increase levels at least 1-0-0, 0-1-0, 0-0-1, or other combinations thereof). In some embodiments, the microalgae composition can be supplemented with nutrients such as, but not limited to, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium. In some embodiments, the supplemented nutrient is not up taken, chelated, or absorbed by the microalgae. In some embodiments, the concentration of the supplemental nutrient can include 1-50 g per 100 g of the composition.

A liquid composition comprising microalgae can be stabilized by heating and cooling in a pasteurization process. As shown in the Examples, the inventors found that the active ingredients of the microalgae based composition maintained effectiveness in at least one characteristic of a plant after being subjected to the heating and cooling of a pasteurization process. In other embodiments, liquid compositions with whole cells or processed cells (e.g., dried, lysed, extracted) of microalgae cells may not need to be stabilized by pasteurization. For example, microalgae cells that have been processed, such as by drying, lysing, and extraction, or extracts can include such low levels of bacteria that a liquid composition can remain stable without being subjected to the heating and cooling of a pasteurization process.

In some embodiments, the composition can be heated to a temperature m the range of 50-70° C. In some embodiments, the composition can be heated to a temperature in the range of 55-65° C. In some embodiments, the composition can be heated to a temperature in the range of 58-62° C. In some embodiments, the composition can be heated to a temperature in the range of 50-60° C. In some embodiments, the composition can be heated to a temperature in the range of 60-70° C. In other aspects of the invention, the composition can be heated to a temperature that is at least 65 degrees C. or higher, such as at least 75 degrees C. or higher, such as at least 80 degrees C. or higher, or at least 90 degrees or higher, such as about 95 degrees C., or the heat can be characterized as being in a range of 50-100 degrees C., such as 60-95 degrees C., e.g., 75-95 degrees C., or 80-, 85-, or 90-95 degrees C.

In some embodiments, the composition can be heated for a time period in the range of 90-150 minutes. In some embodiments, the composition can be heated for a time period in the range of 110-130 minutes. In some embodiments, the composition can be heated for a time period in the range of 90-100 minutes. In some embodiments, the composition can be heated for a time period in the range of 100-110 minutes. In some embodiments, the composition can be heated for a time period in the range of 110-120 minutes. In some embodiments, the composition can be heated for a time period in the range of 120-130 minutes. In some embodiments, the composition can be heated for a time period in the range of 130-140 minutes. In some embodiments, the composition can be heated for a time period in the range of 140-150 minutes.

After the step of heating or subjecting the liquid composition to high temperatures is complete, the compositions can be cooled at any rate to a temperature that is safe to work with. In one non-limiting embodiment, the composition can be cooled to a temperature in the range of 35-45° C. In some embodiments, the composition can be cooled to a temperature m the range of 36-44° C. In some embodiments, the composition can be cooled to a temperature m the range of 37-43° C. In some embodiments, the composition can be cooled to a temperature m the range of 38-42° C. In some embodiments, the composition can be cooled to a temperature m the range of 39-41° C. In further embodiments, the pasteurization process can be part of a continuous production process that also involves packaging, and thus the liquid composition can be packaged (e.g., bottled) directly after the heating or high temperature stage without a cooling step.

In some embodiments, the composition can include 5-30% solids by weight of microalgae cells (i.e., 5-30 g of microalgae cells/100 mL of the liquid composition). In some embodiments, the composition can include 5-20% solids by weight of microalgae cells. In some embodiments, the composition can include 5-15%> solids by weight of microalgae cells. In some embodiments, the composition can include 5-10% solids by weight of microalgae cells. In some embodiments, the composition can include 10-20% solids by weight of microalgae cells. In some embodiments, the composition can include 10-20% solids by weight of microalgae cells. In some embodiments, the composition can include 20-30% solids by weight of microalgae cells. In some embodiments, further dilution of the microalgae cells percent solids by weight can occur before application for low concentration applications of the composition.

In some embodiments, the composition can include less than 1% by weight of microalgae biomass or extracts (i.e., less than 1 g of microalgae derived product/100 mL of the liquid composition). In some embodiments, the composition can include less than 0.9% by weight of microalgae biomass or extracts. In some embodiments, the composition can include less than 0.8% by weight of microalgae biomass or extracts. In some embodiments, the composition can include less than 0.7% by weight of microalgae biomass or extracts. In some embodiments, the composition can include less than 0.6% by weight of microalgae biomass or extracts. In some embodiments, the composition can include less than 0.5% by weight of microalgae biomass or extracts. In some embodiments, the composition can include less than 0.4%> by weight of microalgae biomass or extracts. In some embodiments, the composition can include less than 0.3% by weight of microalgae biomass or extracts. In some embodiments, the composition can include less than 0.2% by weight of microalgae biomass or extracts. In some embodiments, the composition can include less than 0.1% by weight of microalgae biomass or extracts. In some embodiments, the composition can include at least 0.0001% by weight of microalgae biomass or extracts. In some embodiments, the composition can include at least 0.001% by weight of microalgae biomass or extracts. In some embodiments, the composition can include at least 0.01% by weight of microalgae biomass or extracts. In some embodiments, the composition can include at least 0.1% by weight of microalgae biomass or extracts. In some embodiments, the composition can include 0.0001-1% by weight of microalgae biomass or extracts. In some embodiments, the composition can include 0.0001-0.001% by weight of microalgae biomass or extracts. In some embodiments, the composition can include 0.001-0.01<% by weight of microalgae biomass or extracts. In some embodiments, the composition can include 0.01-0.1% by weight of microalgae biomass or extracts. In some embodiments, the composition can include 0.1-1% by weight of microalgae biomass or extracts.

In some embodiments, an application concentration of 0.1% of microalgae biomass or extract equates to 0.04 g of microalgae biomass or extract in 40 mL of a composition. While the desired application concentration to a plant can be 0.1% of microalgae biomass or extract, the composition can be packaged as a 10% concentration (0.4 mL in 40 mL of a composition). Thus a desired application concentration of 0.1% would require 6,000 mL of the 10% microalgae biomass or extract in the 100 gallons of water applied to the assumption of 15,000 plants in an acre, which is equivalent to an application rate of about 1.585 gallons per acre. In some embodiments, a desired application concentration of 0.01% of microalgae biomass or extract using a 10% concentration composition equates to an application rate of about 0.159 gallons per acre. In some embodiments, a desired application concentration of 0.001% of microalgae biomass or extract using a 10% concentration composition equates to an application rate of about 0.016 gallons per acre. In some embodiments, a desired application concentration of 0.0001% of microalgae biomass or extract using a 10% concentration composition equates to an application rate of about 0.002 gallons per acre.

In another non-limiting embodiment, correlating the application of the microalgae biomass or extract on a per plant basis using the assumption of 15,000 plants per acre, the composition application rate of 1 gallon per acre is equal to about 0.25 mL per plant=0.025 g per plant=25 mg of microalgae biomass or extract per plant. The water requirement assumption of 100 gallons per acre is equal to about 35 mL of water per plant. Therefore, 0.025 g of microalgae biomass or extract in 35 mL of water is equal to about 0.071 g of microalgae biomass or extract per 100 mL of composition equates to about a 0.07% application concentration. In some embodiments, the microalgae biomass or extract based composition can be applied at a rate in a range as low as about 0.001-10 gallons per acre, or as high as up to 150 gallons per acre.

In some embodiments, stabilizing means or stabilizers that substantially all or all (at least within the capacity of detection) are not active regarding the improvement of soil and/or plant characteristics, such as with respect to plant germination, emergence, maturation, quality, and yield, but instead aid in stabilizing the composition can be added to prevent the proliferation of unwanted microorganisms (e.g., yeast, mold) and prolong shelf life of the composition. Such inactive but stabilizing means or stabilizers can include an acid that exhibits anti-microbial or otherwise stabilizing properties in the amount that the stabilizing means/stabilizer is present in the composition, such as but not limited to phosphoric acid or citric acid, and a yeast and mold inhibitor, such as but not limited to potassium sorbate. In some embodiments, the stabilizing means are suitable for plants and do not inhibit the growth or health of the plant. In the alternative, the stabilizing means can contribute to nutritional properties of the liquid composition, such as but not limited to, the levels of nitrogen, phosphorus, or potassium.

In some embodiments, the composition can include less than 0.3% phosphoric acid. In some embodiments, the composition can include 0.01-0.3% phosphoric acid. In some embodiments, the composition can include 0.05-0.25% phosphoric acid. In some embodiments, the composition can include 0.01-0.1% phosphoric acid. In some embodiments, the composition can include 0.1-0.2% phosphoric acid. In some embodiments, the composition can include 0.2-0.3% phosphoric acid. In some embodiments, the composition can include less than 0.3% citric acid. In some embodiments, the composition can include 0.01-0.3% citric acid. In some embodiments, the composition can include 0.05-0.25% citric acid. In some embodiments, the composition can include 0.01-0.1% citric acid. In some embodiments, the composition can include 0.1-0.2% citric acid. In some embodiments, the composition can include 0.2-0.3% citric acid.

In some embodiments, the composition can include less than 0.5% potassium sorbate. In some embodiments, the composition can include 0.01-0.5% potassium sorbate. In some embodiments, the composition can include 0.05-0.4/o potassium sorbate. In some embodiments, the composition can include 0.01-0.1% potassium sorbate. In some embodiments, the composition can include 0.1-0.2% potassium sorbate. In some embodiments, the composition can include 0.2-0.3% potassium sorbate. In some embodiments, the composition can include 0.3-0.4% i potassium sorbate. In some embodiments, the composition can include 0.4-0.5% potassium sorbate. In some embodiments, the composition is a liquid and substantially includes of water. In some embodiments, the composition can include 70-99% water. In some embodiments, the composition can include 85-95% water. In some embodiments, the composition can include 70-75% water. In some embodiments, the composition can include 75-80% water. In some embodiments, the composition can include 80-85% water. In some embodiments, the composition can include 85-90 'O water. In some embodiments, the composition can include 90-95% water. In some embodiments, the composition can include 95-99% water. The liquid nature and high-water content of the composition facilitates administration of the composition in a variety of manners, such as but not limit to: flowing through an irrigation system, flowing through an above ground drip irrigation system, flowing through a buried drip irrigation system, flowing through a central pivot irrigation system, sprayers, sprinklers, and water cans.

In some embodiments, the liquid composition can be used immediately after formulation, or can be stored in containers for later use. In some embodiments, the composition can be stored out of direct sunlight. In some embodiments, the composition can be refrigerated. In some embodiments, the composition can be stored at 1-10° C. In some embodiments, the composition can be stored at 1-3° C. In some embodiments, the composition can be stored at 3-5° C. In some embodiments, the composition can be stored at 5-8° C. In some embodiments, the composition can be stored at 8-10° C.

In some embodiments, administration of the liquid composition to a seed or plant can be m an amount effective to produce an enhanced characteristic in plants compared to a substantially identical population of untreated seeds or plants. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased fruit yield, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease, improved color, reduced insect damage, reduced blossom end rot, and reduced sun burn. Such enhanced characteristics can occur individually in a plant, in soil, or in combinations of multiple enhanced characteristics.

In some embodiments, after harvest of the microalgae from the culturing vessel, the microalgae biomass can be dried or dehydrated to form a composition of dried microalgae biomass (i.e., reduced moisture content). The microalgae biomass can be dried by at least one method selected from the group consisting of: freeze drying (or lyophilization), drum (or rotary) drying, spray drying, crossflow air drying, solar drying, vacuum shelf drying, pulse combustion drying, flash drying, furnace drying, belt conveyor drying, and refractance window drying. In some embodiments, the microalgae cells can be dried by a combination of two or more methods, such as in a process with multiple drying methods in series. The process of drying the microalgae biomass can reduce the percent moisture (on a wet basis) to the range of about 1-15<% and result in a cake, flakes, or a powder, which is more uniform and more stable than the wet culture of microalgae. In some embodiments, the dried microalgae cells can be intact. In some embodiments, the dried microalgae cells can be lysed or disrupted. In some embodiments, the microalgae cells can be lysed or disrupted prior to or after drying by mechanical, electrical, acoustic, or chemical means. In some embodiments, drying the microalgae cells achieves an acceptable product stability for storage, with the reduction or elimination of chemical stabilizers. The composition can be stored in any suitable container such as, but not limited to, a bag, bucket, jug, tote, or bottle.

In some embodiments, the dried microalgae biomass can have a moisture content of 1-15% on a wet basis. In some embodiments, the dried microalgae biomass can have a moisture content of 1-2% on a wet basis. In some embodiments, the dried microalgae biomass can have a moisture content of 2-3% on a wet basis. In some embodiments, the dried microalgae biomass can have a moisture content of 3-5% on a wet basis. In some embodiments, the dried microalgae biomass can have a moisture content of 5-7% on a wet basis. In some embodiments, the dried microalgae biomass can have a moisture content of 7-10% on a wet basis. In some embodiments, the dried microalgae biomass can have a moisture content of 10-12% on a wet basis. In some embodiments, the dried microalgae biomass can have a moisture content of 12-15% on a wet basis. In some embodiments, the dried microalgae biomass can have a moisture content of 1-8% i on a wet basis. In some embodiments, the dried microalgae biomass can have a moisture content of 8-15% on a wet basis.

The various drying processes can have different capabilities such as, but not limited to, the amount of moisture that can be removed, the preservation of metabolites (e.g., proteins, lipids, pigments, carbohydrates, polysaccharides, soluble nitrogen, phytohormones), and the effect on the cell wall or membrane. For example, loss of protein in *Spirulina* biomass has been found to increase proportionally as the drying temperature increases. Additionally, drying at high temperatures has been shown to alter polymer chains, alter interactions between polysaccharide and glycoprotein, and increase bound water content of polysaccharides. Pigments and fatty acids are also known to oxidize and de-stabilize to different degrees in different drying processes. The effectiveness of each drying method can also vary based on the microalgae species due to different physical characteristics of the microalgae (e.g., sheer sensitivity, cell size, cell wall thickness and composition). The method of drying and drying method parameters can also result in a structural change to the microalgae cell such as, but not limited to, increased porosity in the cell wall, changes in the cell wall make up or bonds, and measurable changes in cell characteristics (e.g., elasticity, viscosity, digestibility); as wells as functional differences when applied to plants that can be measured in changes in plant performance or plant characteristics. Drying microalgae with a combination of methods in series can also result in structural and functional changes, minimize structural and functional changes, or increase the effectiveness for a particular type of microalgae.

Drum drying includes the use of sloped, rotating cylinders which use gravity to move the microalgal biomass from one end to the other. Drum drying can be conducted with direct contact between a hot gas and the microalgal biomass, or indirect heating in which the gas and microalgal biomass is separated by a barrier such as a steel shell. A non-limiting example of a drum drying process for *Scenedesmus* can include 10 seconds of heating at 120° C. Possible effects to the microalga biomass in a drum drying process include sterilization of the biomass, and breaking of the cell wall. Microalgal biomass that is drum dried can have higher digestibility than microalgal biomass that is spray dried.

Freeze drying includes freezing the microalgal biomass and then transferring the frozen biomass to a vacuum chamber with reduced pressure (e.g., 4.6 Torr). The ice in the microalgal biomass changes to vapor through sublimation which is collected on an extremely cold condenser and removed from the vacuum chamber. Freeze drying typically minimizes the degradation of unsaturated fatty acids and pigments (e.g., carotenoids) through oxidation, which preserves the nutritional value of the microalgal biomass. Although the targeted removal of water in the freeze drying process is beneficial, the process is very costly and time consuming which makes freeze drying impractical for many commercial applications. In some embodiments, microalgae dried by freeze drying can include 2-6% moisture (on a wet basis). A non-limiting example of a freeze drying process for *Scenedesmus* can include 24 hours at −84° C. Freeze drying is known to maintain the integrity of the microalgal cell, but is also known been known in some cases to disrupt the cell or increase the pore size in the cell wall. In *Scenedesmus*, freeze drying was found to decrease rigidity, increase surface area by 165% i, and increase pore size by 19% i of the cells (see eSEM images below). In *Phaeodactylum ricornutum*, freeze drying had no effect on the total lipid content, made the cells more susceptible to lipolysis (i.e., breakdown of lipids, hydrolysis of triglycerides into glycerol and free fatty acids) upon storage than spray dried cells, and made the cells less susceptible to oxidation than spray dried cells.

Spray drying includes atomizing an aqueous microalgae culture into droplets sprayed downwardly in a vertical tower through which hot gases pass downward. The gas stream can be exhausted through a cyclonic separator. The process of spray drying is expensive, but slightly cheaper than freeze drying. Spray drying has become the method of choice for high value products (>$1,000/ton). With the proper type of burner, oxygen can be virtually eliminated from the recycled drying gas, which prevents the oxidation of oxygen sensitive products (e.g., carotenoids). In some embodiments, microalgae dried by spray drying can include 1-7% moisture (on a wet basis). Examples of spray drying systems include: box dryers, tall-form spray dryers, fluidized bed dryers, and moving fluidized bed dryers (e.g., FilterMat spray dryer GEA Process Engineering Inc.). An open cycle spray dryer with a particular direct fired air heater can operate at elevated temperatures (e.g., 60-93° C.) and high oxygen concentrations (e.g., 19-20%). The possible effects of spray drying on microalgal biomass include rupturing the cells walls, reduction of protein content by 10-15%, significant deterioration of pigments (depending on the oxygen concentration), and a lower digestibility than drum drying. In *Phaeodactylum ricornutum*, spray drying had no effect on the total lipid content, made the cells less susceptible to lipolysis than freeze drying, and made the cells more susceptible to oxidation than freeze drying (possibly due to the breakdown of protective carotenoids).

Crossflow air drying uses movement of heated air across a layer of microalgae on a tray, which is a modification of indirect solar and convection oven driers. Crossflow air drying is faster than solar drying, cheaper than drum drying, and is known to typically not break the microalgal cell wall. In some embodiments, microalgae dried by crossflow air drying can include 8-12% moisture (on a wet basis). Non-limiting examples of crossflow air drying for *Spirulina* can include: 1) a temperature of 62° C. for 14 hours, 2) a temperature of 50-60° C., a relative humidity of 7-10%, an air velocity of 1.5 m/s, and a duration of 150-220 minutes, 3) a temperature of 40-60° C. and an air velocity of 1.9-3.8 m/s, and 4) temperatures of 50-70° C. for layers of 3-7 mm in a perforated tray with parallel air flow. Crossflow air drying of *Spirulina* has shown a loss in protein of about 17% and a loss in phycocyanin of 37-50%. Particularly, degradation of phycocyanin was found to occur above 60° C., but there was no significant change in the fatty acid composition in the crossflow air drying methods.

Non-limiting examples of crossflow air drying of *Chlorella* kessleri and *Chlamydomonas reinhardtii* can include a temperature of 55° C. for more than 5 hours. Crossflow air drying of *Chlorella* kessleri and *Chlamydomonas reinhardtii* has produced a reduction of chlorophyll relative to the dry cell weight, an increase of total fatty acid content relative to the dry cell, a decrease of polar lipids relative to the dry cell weight, and a decrease in the availability of nutritional salts (e.g., S, N). A cell's sensitivity to air drying stress (as measured through the change in chlorophyll) can be correlated to the properties of the cell wall. For example, the crossflow air dried *Chlamydomonas reinhardtii* (hydroxyproline-rich glucoprotein based cell walls) had a larger decrease in chlorophyll than the *Chlorella* kessleri (sugar based cell walls), which can be associated with the cell wall's ability to restructure in S and N deficient conditions. In a non-limiting example of drying 5-7 mm thick layers of *Aphanothece microscopica nagai* at temperatures of 40-60° C. with parallel air flow of 1.5 m/s, it was found that drying conditions influenced the concentrations of protein, carbohydrates, and lipids in the biomass.

Solar drying methods can include the use of direct solar radiation to dry microalgae on sand or a plastic sheet, or the indirect use of solar radiation to heat air that is circulated around microalgae in a dryer. Direct solar drying is strongly weather dependent, slow, and can require a short duration of high heat (e.g., 120° C.) to increase the biological value of the microalgal biomass. A non-limiting example of a direct solar drying process for *Scenedesmus* can include a 1,500 micron thickness white plastic drying bed liner, a temperature of 25-30° C., and a duration of 72 hours. The possible effects of direct solar drying on microalgal biomass include chlorophyll degradation, overheating of the biomass, and creation of an unpleasant odor. Indirect solar drying prevents overheating, has a higher drying rate than direct solar drying, but produces a less attractive profile in the final product. An indirect solar drying method for microalgae can include temperature of 65-70° C. for 0.5-6 hours.

Drying of a thin film of microalgal biomass in a convection oven is a fairly common practice performed in scientific literature to test the biomass going through further processing, but may be less practical for many commercial applications. Thin film convection oven drying has been demonstrated in the literature with species of *Chlorella, Chlamydomonas*, and *Scenedesmus*. In some embodiments, microalgae dried by oven drying can include 6-10% moisture (on a wet basis). Thin film convection oven drying methods can include temperatures of 30-90° C., and durations of 4-12 hours. Thin film convection oven dried microalgal biomass showed no significant change in the fatty acid profile and a slight decrease in the degree of unsaturation of fatty acids at higher temperature for ruptured cells (likely due to oxidation causing cleavage of unsaturated bonds).

Microalgae can be dried in thin layers with heat at a reduced pressure. Non-limiting examples of drying of *Spirulina* in layers within a vacuum can include temperatures of 50-650 C and a pressure of 0.05-0.06 atm. Possible effects on the microalgae that may result from vacuum shelf drying include development of a hygroscopic property (i.e., ability to attract and hold water particles from the surrounding environment by absorption or adsorption) and development of a porous structure.

Pulse combustion drying uses a blast of controlled heat to flash dry the microalgae. Air is pumped into a combustion chamber, mixed with a fuel and ignited to created pressurized hot gas (e.g., at 3 psi). The dryer can automatically blast the heated gas with quench air to control the temperature of the heated gas before coming into contact with the microalgae. The process is then repeated multiple times to provide the pulses of heated gas. Pulse combustion heating is known to dry microalgae at a low heat which preserves the integrity and nutritional value of the microalgae. Flash drying includes spraying or injecting a mixture of dried and undried material into a hot gas stream, and is commonly used in wastewater sludge drying.

Drying of microalgae using an incinerator or furnace can include heating the biomass to a high temperature (e.g., 100° C.) to evaporate the water. The heating can be performed at a level below the temperature at which the microalgae will burn and can include using hot gases that proceed downwardly with the biomass in parallel flow. Microalgae that are dewatered to an appropriate solids level can be dried indirectly by heating elements lining the pathway of a belt conveyor. Refractance window drying is a dehydration method that uses infra-red light, rather than high direct temperature, to remove moisture from microalgae. \Vet microalgae biomass can be translated through an evaporation chamber by a belt disposed above a circulating hot water reservoir to dry the microalgae with infra-red energy in a refractance window drying. In some embodiments, microalgae dried by refractance window drying can include 3-8% moisture (on a wet basis).

In some embodiments, the dry composition can be mixed with water and stabilized by heating and cooling in a pasteurization process, adjustment of pH, the addition of an inhibitor of yeast and mold growth, or combinations thereof. In one non-limiting example of preparing the dried microalgae composition for application to plants, the microalgae harvested from the culturing system is first held in a harvest tank before centrifuging the culture. Once the microalgae is centrifuged, the centrifuge discharges the fraction rich in microalgae whole cell solids, but also containing the accompanying constituents from the culture medium, into a container at a temperature of about 30° C. The microalgae composition is then dried.

Surprisingly, the inventors found that administration of the described composition in low concentration applications was effective in producing enhanced characteristics in plants. In some embodiments, a liquid composition can be administered before the seed is planted. In some embodiments, a liquid composition can be administered at the time the seed is planted. In some embodiments, a liquid composition can be administered after the seed is planted. In some embodiments, a liquid composition can be administered to plants that have emerged from the ground. In some embodiments, a dried composition can be applied to the soil before, during, or after the planting of a seed. In some embodiments, a dried composition can be applied to the soil before or after a plant emerges from the soil.

In some embodiments, the volume or mass of the microalgae based composition applied to a seed, seedling, or plant may not increase or decrease during the growth cycle of the plant (i.e., the amount of the microalgae composition applied to the plant will not change as the plant grows larger). In some embodiments, the volume or mass of the microalgae based composition applied to a seed, seedling, or plant can increase during the growth cycle of the plant (i.e., applied on a mass or volume per plant mass basis to provide more of the microalgae composition as the plant grows larger). In some embodiments, the volume or mass of the microalgae based composition applied to a seed, seedling, or plant can decrease during the growth cycle of the plant (i.e., applied on a mass or volume per plant mass basis to provide more of the microalgae composition as the plant grows larger).

Seed Soak Application

In one non-limiting embodiment, the administration of the liquid composition can include soaking the seed in an effective amount of the liquid composition before planting the seed. In some embodiments, the administration of the liquid composition further includes removing the seed from the liquid composition after soaking, and drying the seed before planting. In some embodiments, the seed can be soaked in the liquid composition for a time period in the range of 90-150 minutes. In some embodiments, the seed can be soaked in the liquid composition for a time period in the range of 110-130 minutes. In some embodiments, the seed can be soaked in the liquid composition for a time period in the range of 90-100 minutes. In some embodiments, the seed can be soaked in the liquid composition for a time period in the range of 100-110 minutes. In some embodiments, the seed can be soaked in the liquid composition for a time period in the range of 110-120 minutes. In some embodiments, the seed can be soaked in the liquid composition for a time period in the range of 120-130 minutes. In some embodiments, the seed can be soaked in the liquid composition for a time period in the range of 130-140 minutes. In some embodiments, the seed can be soaked in the liquid composition for a time period in the range of 140-150 minutes.

The composition can be diluted to a lower concentration for an effective amount in a seed soak application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae source components in the diluted composition can be calculated by the multiplying the original grams of microalgae sourced components per 100 mL by the ratio of the volume of the composition to the volume of water.

Soil Application—Seed

In another non-limiting embodiment, the administration of the composition can include contacting the soil in the immediate vicinity of the planted seed with an effective amount of the composition. In some embodiments, the liquid composition can be supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The percent solids of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition m a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre (such as 0.02-8 gal/acre, such as 0.025-7.5 gal/acre, 0.05-5 gal/acre, 0.1-5 gal/acre, 0.2-5 gal/acre, 0.2-4 gal/acre, 0.25-4 gal/acre, 0.33-3 gal/acre, 0.5-2.5 gal/acre, 0.5-2 gal/acre, or 0.66- or 0.75-1, 1.5, 1.75, or 2 gal/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre (such as 0.25-1 gal/acre, 0.33-1 gal/acre, 0.5-1 gal/acre, or 0.25-0.75 gal/acre, or 0.33-0.66 gal/acre). In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 2-20 liters/acre. In some embodiments, the rate of application of the liquid composition in a soil application can include a rate in the range of 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

Capillary Action Application

In another non-limiting embodiment, the administration of the liquid composition can include first soaking the seed in water, removing the seed from the water, drying the seed, applying an effective amount of the liquid composition below the seed planting level in the soil, and planting the seed, wherein the liquid composition supplied to the seed from below by capillary action. In some embodiments, the seed can be soaked in water for a time period in the range of 90-150 minutes. In some embodiments, the seed can be soaked in water for a time period in the range of 110-130 minutes. In some embodiments, the seed can be soaked in water for a time period in the range of 90-100 minutes. In some embodiments, the seed can be soaked in water for a time period in the range of 100-110 minutes. In some embodiments, the seed can be soaked in water for a time period in the range of 110-120 minutes. In some embodiments, the seed can be soaked in water for a time period in the range of 120-130 minutes. In some embodiments, the seed can be soaked in water for a time period in the range of 130-140 minutes. In some embodiments, the seed can be soaked in water for a time period in the range of 140-150 minutes.

Hydroponic Applications

In another non-limiting embodiment, the administration of the liquid composition to a seed or plant can include applying the microalga based composition in combination with a nutrient medium to seeds disposed in and plants growing in a hydroponic growth medium or an inert growth medium (e.g., coconut husks). The liquid composition can be applied multiple times per day, per week, or per growing season.

Foliar Application

In one non-limiting embodiment, the administration of the composition can include contacting the foliage of the plant with an effective amount of the composition. In some embodiments, the liquid composition can be sprayed on the foliage by a hand sprayer, a sprayer on an agriculture implement, or a sprinkler.

The composition can be diluted to a lower concentration for an effective amount in a foliar application by mixing a volume of the composition in a volume of water. The concentration of microalgae sourced components resulting in the diluted composition can be calculated by the multiplying the original concentration in the composition by the ratio of the volume of the composition to the volume of water. Alternatively, the grams of microalgae sourced components in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a foliar application can include a rate in the range of 10-50 gallons/acre. In some embodiments, the rate of application of the liquid composition in a foliar application can include a rate in the range of 10-15 gallons/acre. In some embodiments, the rate of application of the liquid composition in a foliar application can include a rate in the range of 15-20 gallons/acre. In some embodiments, the rate of application of the liquid composition in a foliar application can include a rate in the range of 20-25 gallons/acre. In some embodiments, the rate of application of the liquid composition in a foliar application can include a rate in the range of 25-30 gallons/acre. In some embodiments, the rate of application of the liquid composition in a foliar application can include a rate in the range of 30-35 gallons/acre. In some embodiments, the rate of application of the liquid composition in a foliar application can include a rate in the range of 35-40 gallons/acre. In some embodiments, the rate of application of the liquid composition in a foliar application can include a rate in the range of 40-45 gallons/acre. In some embodiments, the rate of application of the liquid composition in a foliar application can include a rate in the range of 45-50 gallons/acre.

In some embodiments, the rate of application of the liquid composition in a foliar application can include a rate in the range of 0.01-10 gallons/acre. In some embodiments, the rate of application of the liquid composition in a foliar application can include a rate in the range of 0.01-0.1 gallons/acre. In some embodiments, the rate of application of the liquid composition in a foliar application can include a rate in the range of 0.1-1.0 gallons/acre. In some embodiments, the rate of application of the liquid composition in a foliar application can include a rate in the range of 1-2 gallons/acre. In some embodiments, the rate of application of the liquid composition in a foliar application can include a rate in the range of 2-3 gallons/acre. In some embodiments, the rate of application of the liquid composition in a foliar application can include a rate in the range of 3-4 gallons/acre. In some embodiments, the rate of application of the liquid composition in a foliar application can include a rate in the range of 4-5 gallons/acre. In some embodiments, the rate of application of the liquid composition in a foliar application can include a rate in the range of 5-10 gallons/acre.

The frequency of the application of the composition can be expressed as the number of applications per period of time (e.g., two applications per month), or by the period of time between applications (e.g., one application every 21 days). In some embodiments, the plant can be contacted by the composition in a foliar application every 3-28 days, such as every 3-21 days, every 3-15 days, every 5-15 days, every 7-14 days, or every 6-12 days. In some embodiments, the plant can be contacted by the composition in a foliar application every 4-10 days, such as every 4-8 days, such as every 5-7 days. In some embodiments, the plant can be contacted by the composition in a foliar application every 18-24 days. In some embodiments, the plant can be contacted by the composition in a foliar application every 3-7 days. In some embodiments, the plant can be contacted by the composition in a foliar application every 7-14 days. In some embodiments, the plant can be contacted by the composition in a foliar application every 14-21 days. In some embodiments, the plant can be contacted by the composition in a foliar application every 21-28 days.

Foliar application(s) of the composition generally begin after the plant has become established, but can begin before establishment, at defined time period after planting, or at a defined time period after emergence form the soil in some embodiments. In some embodiments, the plant can be first contacted by the composition in a foliar application 5-14 days after the plant emerges from the soil. In some embodiments, the plant can be first contacted by the composition in a foliar application 5-7 days after the plant emerges from the soil. In some embodiments, the plant can be first contacted by the composition in a foliar application 7-10 days after the plant emerges from the soil. In some embodiments, the plant can be first contacted by the composition in a foliar application 10-12 days after the plant emerges from the soil. In some embodiments, the plant can be first contacted by the composition in a foliar application 12-14 days after the plant emerges from the soil.

Soil Application—Plant

In another non-limiting embodiment, the administration of the composition can include contacting the soil in the immediate vicinity of the plant with an effective amount of the composition. In some embodiments, the liquid composition can be supplied to the soil by injection into to a low volume irrigation system, such as but not limited to a drip irrigation system supplying water beneath the soil through perforated conduits or at the soil level by fluid conduits hanging above the ground or protruding from the ground. In some embodiments, the liquid composition can be supplied to the soil by a soil drench method wherein the liquid composition is poured on the soil.

The composition can be diluted to a lower concentration for an effective amount in a soil application by mixing a volume of the composition in a volume of water. The concentration of microalgae sourced components resulting in the diluted composition can be calculated by the multiplying the original concentration of microalgae sourced components in the composition by the ratio of the volume of the composition to the volume of water. Alternatively, the grams of microalgae cells in the diluted composition can be calculated by the multiplying the original grams of microalgae sourced components per 100 mL by the ratio of the volume of the composition to the volume of water.

The rate of application of the composition at the desired concentration can be expressed as a volume per area. In some embodiments, the rate of application of the liquid composition in a soil application can include a rate in the range of 50-150 gallons/acre. In some embodiments, the rate of application of the liquid composition in a soil application can include a rate in the range of 75-125 gallons/acre. In some embodiments, the rate of application of the liquid composition in a soil application can include a rate in the range of 50-75 gallons/acre. In some embodiments, the rate of application of the liquid composition in a soil application can include a rate in the range of 75-100 gallons/acre. In some embodiments, the rate of application of the liquid composition in a soil application can include a rate in the range of 100-125 gallons/acre. In some embodiments, the rate of application of the liquid composition in a soil application can include a rate in the range of 125-150 gallons/acre.

In some embodiments, the rate of application of the liquid composition in a soil application can include a rate in the range of 10-50 gallons/acre. In some embodiments, the rate of application of the liquid composition in a soil application can include a rate in the range of 10-20 gallons/acre. In some embodiments, the rate of application of the liquid composition in a soil application can include a rate in the range of 20-30 gallons/acre. In some embodiments, the rate of application of the liquid composition in a soil application can include a rate in the range of 30-40 gallons/acre. In some embodiments, the rate of application of the liquid composition in a soil application can include a rate in the range of 40-50 gallons/acre.

In some embodiments, the rate of application of the liquid composition in a soil application can include a rate in the range of 0.01-10 gallons/acre. In some embodiments, the rate of application of the liquid composition in a soil application can include a rate in the range of 0.01-0.1 gallons/acre. In some embodiments, the rate of application of the liquid composition in a soil application can include a rate in the range of 0.1-1.0 gallons/acre. In some embodiments, the rate of application of the liquid composition in a soil application can include a rate in the range of 1-2 gallons/acre. In some embodiments, the rate of application of the liquid composition in a soil application can include a rate in the range of 2-3 gallons/acre. In some embodiments, the rate of application of the liquid composition in a soil application can include a rate in the range of 3-4 gallons/acre. In some embodiments, the rate of application of the liquid composition in a soil application can include a rate in the range of 4-5 gallons/acre. In some embodiments, the rate of application of the liquid composition in a soil application can include a rate in the range of 5-10 gallons/acre.

In some embodiments, the rate of application of the liquid composition in a soil application can include a rate in the range of 0.5-20 liters/acre, such as 0.75-15 liters/acre, 1-12 liters/acre, 1.5-10 liters/acre, 2-10 liters/acre, 2-15 liters/acre, 2-20 liters/acre, 3-12 liters/acre, 3-10 liters/acre, 4-10 liters/acre, 4-12 liters/acre, or 5-10 liters/acre. In some embodiments, the rate of application of the liquid composition in a soil application can include a rate in the range of 3.5-15 liters/acre such as 3.7-15 liters/acre. In some embodiments, the rate of application of the liquid composition in a soil application can include a rate in the range of 2-5 liters/acre. In some embodiments, the rate of application of the liquid composition in a soil application can include a rate in the range of 5-10 liters/acre. In some embodiments, the rate of application of the liquid composition in a soil application can include a rate in the range of 10-15 liters/acre. In some embodiments, the rate of application of the liquid composition in a soil application can include a rate in the range of 15-20 liters/acre.

The frequency of the application of the composition can be expressed as the number of applications per period of time (e.g., two applications per month), or by the period of time between applications (e.g., one application every 21 days). In some embodiments, the plant can be contacted by the composition in a soil application every 3-28 days. In some embodiments, the plant can be contacted by the composition in a soil application every 4-10 days, but in other aspects application is every 14 days, every 21 days, or every 28 days. In some embodiments, the plant can be contacted by the liquid composition in a soil application every 18-24 days or every 14-35 days. In some embodiments, the plant can be contacted by the composition in a soil application every 3-7 days. In some embodiments, the plant can be contacted by the composition in a soil application every 7-14 days. In some embodiments, the plant can be contacted by the composition in a soil application every 14-21 days. In some embodiments, the plant can be contacted by the composition in a soil application every 21-28 days.

Soil application(s) of the composition generally begin after the plant has become established, but can begin before establishment, at defined time period after planting, or at a defined time period after emergence form the soil in some embodiments. In some embodiments, the plant can be first contacted by the composition in a soil application 5-14 days after the plant emerges from the soil. In some embodiments, the plant can be first contacted by the composition in a soil application 5-7 days after the plant emerges from the soil. In some embodiments, the plant can be first contacted by the liquid composition in a soil application 7-10 days after the plant emerges from the soil. In some embodiments, the plant can be first contacted by the composition in a soil application 10-12 days after the plant emerges from the soil. In some embodiments, the plant can be first contacted by the composition in a soil application 12-14 days after the plant emerges from the soil.

Whether in a seed soak, soil, capillary action, foliar, or hydroponic application the method of use includes relatively low concentrations of the composition. Even at such low concentrations, the described composition has been shown to be effective at producing an enhanced characteristic in plants. The ability to use low concentrations allows for a reduced impact on the environment that may result from over application and an increased efficiency in the method of use of the composition by requiring a small amount of material to produce the desired effect. In some embodiments, the use of the liquid composition with a low volume irrigation system in soil applications allows the low concentration of the liquid composition to remain effective and not be diluted to a point where the composition is no longer in at a concentration capable of producing the desired effect on the plants while also increasing the grower's water use efficiency.

In conjunction with the low concentrations of microalgae cells in the composition necessary to be effective for enhancing the described characteristics of plants, the composition does not have be to administered continuously or at a high frequency (e.g., multiple times per day, daily). The ability of the composition to be effective at low concentrations and a low frequency of application was an unexpected result, due to the traditional thinking that as the concentration of active ingredients decreases the frequency of application should increase to provide adequate amounts of the active ingredients. Effectiveness at low concentration and application frequency increases the material usage efficiency of the method of using the composition while also increasing the yield efficiency of the agricultural process.

Administration of a dry composition treatment to the soil, seed, or plant can be in an amount effective to produce an enhanced characteristic in the plant compared to a substantially identical population of untreated plant. Such enhanced characteristics can include accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased flowering, increased fruit yield, increased fruit growth, and increased fruit quality. Non-limiting examples of such enhanced characteristics can include accelerated achievement of the hypocotyl stage, accelerated protrusion of a stem from the soil, accelerated achievement of the cotyledon stage, accelerated leaf formation, increased leaf size, increased leaf area index, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased root mass (indicator of plant health), increased shoot weight (indicator of plant health), increased plant height, increased thatch height, increased resistance to salt stress, increased plant resistance to heat stress (temperature stress), increased plant resistance to heavy metal stress, increased plant resistance to drought, increased plant resistance to disease improved color, reduced insect damage, reduced blossom end rot, and reduced sun burn. Such enhanced characteristics can occur individually in a plant, or in combinations of multiple enhanced characteristics. The characteristic of flowering has is important for not only the ornamental market, but also for fruiting plants where an increase in flowering can correlate to an increase in fruit production.

Seed Coating

In one non-limiting embodiment, the administration of the dried microalgae composition treatment can include coating a seed. In some embodiments, a seed can be coated by passing through a slurry comprising microalgae and then dried. In some embodiments, the seed can be coated with the dried microalgae composition and other components such as, but not limited to, binders and fillers known in the art to be suitable for coating seeds. The fillers can include suitable inorganic particles such as, but not limited to, silicate particles, carbonate particles, and sulphate particles, quartz, zeolites, pumice, perlite, diatomaceous earth, pyrogene silica, $Sb_2O_3$, $TiO_2$, lithopone, ZnO, and hydrated aluminum oxide. The binders can include, but are not limited to, water-soluble polymers, polyvinyl acetate, polyvinyl alcohol, polyvinyl pyrrolidone, polyurethane, methyl cellulose, carboxymethyl cellulose, hydroxylpropyl cellulose, sodium alginate, polyacrylate, casein, gelatin, pullulan, polyacrylamide, polyethylene oxide, polystyrene, styrene acrylic copolymers, styrene butadiene polymers, poly (N-vinylacetamide), waxes, canauba wax, paraffin wax, polyethylene wax, bees wax, polypropylene wax, and ethylene vinyl acetate. In some embodiments, the seed coating can include a wetting and dispersing additive such as, but not limited to polyacrylates, organo-modified polyacrylates, sodium polyacrylates, polyurethanes, phosphoric acid esters, star polymers, and modified polyethers.

In some embodiments, the seed coating can include other components such as, but not limited to, a solvent, thickener, coloring agent, anti-foaming agent, biocide, surfactant, and pigment. In some embodiments, the seed coating can include a hydrogel or film coating materials. In some embodiments, the concentration of dried microalgae in the seed coating can include 0.001-20% solids, such as 0.01%-15% solids, such as 0.25%-12% solids, for example 1%-12.5% solids, 2.5%-15% solids, 2.5%-12.5% solids, 3-12% solids, 5-12% solids, 5-15% solids, 7.5-12.5% solids, 8-12%> solids, or 9-11% solids, such as about 10% solids. In some embodiments, the concentration of microalgae in the seed coating can include less than 0.1% solids. In some embodiments, the concentration of dried microalgae in the seed coating can include 0.001-0.01% solids. In some embodiments, the concentration of dried microalgae in the seed coating can include 0.01-0.1% solids. In some embodiments, the concentration of dried microalgae in the seed coating can include 0.1-1% solids. In some embodiments, the concentration of dried microalgae in the seed coating can include 1-2% solids. In some embodiments, the concentration of dried microalgae in the seed coating can include 2-3% solids. In some embodiments, the concentration of dried microalgae in the seed coating can include 3-5% solids. In some embodiments, the concentration of dried microalgae in the seed coating can include 5-10% solids. In some embodiments, the concentration of dried microalgae in the seed coating can include 10-15% solids. In some embodiments, the concentration of dried microalgae in the seed coating can include 15-20% solids. In some embodiments, the seed can be coated in a single step. In some embodiments, the seed can be coated in multiple steps. Conventional or otherwise suitable coating equipment or techniques can be used to coat the seeds. Suitable equipment can include drum coaters, fluidized beds, rotary coaters, side vended pan, tumble mixers, and spouted beds. Suitable techniques can include mixing in a container, tumbling, spraying, or immersion. After coating, the seeds can be dried or partially dried.

Soil Application

In another non-limiting embodiment, the administration of the dried microalgae composition treatment can include mixing an effective amount of the composition with a solid growth medium, such as soil, potting mix, compost, or inert hydroponic material, prior to planting a seed, seedling, or plant in the solid growth medium. The dried microalgae composition can be mixed in the solid growth medium at an inclusion level of 0.001-20% by volume. In some embodiments, the effective amount in a mixed solid growth medium application of the dried microalgae composition can include a concentration in the range of 0.001-0.01% solids. In some embodiments, the effective amount in a mixed solid growth medium application of the dried microalgae composition can include a concentration in the range of 0.01-0.1% solids. In some embodiments, the effective amount in a mixed solid growth medium application of the dried microalgae composition can include a concentration in the range of 0.1-1% solids. In some embodiments, the effective amount in a mixed solid growth medium application of the dried microalgae composition can include a concentration in the range of 1-3%% solids. In some embodiments, the effective amount in a mixed solid growth medium application of the dried microalgae composition can include a concentration in the range of 3-5% solids. In some embodiments, the effective amount in a mixed solid growth medium application of the dried microalgae composition can include a concentration in the range of 5-10% solids. In some embodiments, the effective amount in a mixed solid growth medium application of the dried microalgae composition can include a concentration in the range of 10-20% solids.

In another non-limiting embodiment, the administration of the dried microalgae composition treatment can include inclusion in a solid growth medium during in-furrow plants or broadcast application to the ground. The dried microalgae composition can be applied at a rate of 50-500 grams/acre. In some embodiments, the application rate of the dried microalgae composition can include 50-100 grams/acre. In some embodiments, the application rate of the dried microalgae composition can include 100-150 grams/acre. In some embodiments, the application rate of the dried microalgae composition can include 150-200 grams/acre. In some embodiments, the application rate of the dried microalgae composition can include 200-250 grams/acre. In some embodiments, the application rate of the dried microalgae composition can include 250-300 grams/acre. In some embodiments, the application rate of the dried microalgae composition can include 300-350 grams/acre. In some embodiments, the application rate of the dried microalgae composition can include 350-400 grams/acre. In some embodiments, the application rate of the dried microalgae composition can include 400-450 grams/acre. In some embodiments, the application rate of the dried microalgae composition can include 450-500 grams/acre.

The dried microalgae composition can be applied at a rate of 10-50 grams/acre. In some embodiments, the application rate of the dried microalgae composition can include 10-20 grams/acre. In some embodiments, the application rate of the dried microalgae composition can include 20-30 grams/acre. In some embodiments, the application rate of the dried microalgae composition can include 30-40 grams/acre. In some embodiments, the application rate of the dried microalgae composition can include 40-50 grams/acre.

The dried microalgae composition can be applied at a rate of 0.001-10 grams/acre. In some embodiments, the application rate of the dried microalgae composition can include 0.001-0.01 grams/acre. In some embodiments, the application rate of the dried microalgae composition can include 0.01-0.1 grams/acre. In some embodiments, the application rate of the dried microalgae composition can include 0.1-1.0 grams/acre. In some embodiments, the application rate of the dried microalgae composition can include 1-2 grams/acre. In some embodiments, the application rate of the dried microalgae composition can include 2-3 grams/acre. In some embodiments, the application rate of the dried microalgae composition can include 3-4 grams/acre. In some embodiments, the application rate of the dried microalgae composition can include 4-5 grams/acre. In some embodiments, the application rate of the dried microalgae composition can include 5-10 grams/acre.

In another aspect, the invention provides a method of promoting an increase in the growth of a plant, comprising administering an effective amount of a composition of the invention to a plant such that growth of the treated plant is at least about 10% more than what is achieved by a control. In some cases the increase of growth is 15% or more, such as 20% or more, 25% or more, 30% or more, 35% or more, or even 40% or more (e.g., at least 45%, at least 50%, at least 55%, at least 60%, at least 65%, at least 70%, or even at least 75% increase in growth). In some aspects an effective amount to stimulate growth comprises administering a composition comprising a concentration of a microalgae composition (such as a whole cell microalgae, a post-extraction microalgae biomass, or a combination thereof) that is in a concentration of 0.001%-0.1%, such as 0.0025%-0.1%, for example 0.005%-0.1%, 0.0075%-0.1%, 0.01%-0.1%, e.g., 0.01%-0.025%, 0.01%-0.05%, 0.01%-0.075%, or 0.001%-0.025%, 0.001%-0.05%, 0.02%-0.08%, or 0.025%-0.075%. In one aspect, the microalgae composition comprises an *Aurantiochytrium* composition. In one aspect, the microalgae composition comprises a post-extraction *Aurantiochytrium* composition, such as a composition in which at least about 25%, at least about 33%, at least about 50%, at least about 75%, or even more (e.g., at least about 85%, 90%, or 95%), of the DHA and DHA-associated lipids of the *Aurantiochytrium* whole cell composition have been extracted from the biomass prior to the inclusion m the composition.

In another aspect, the invention provides a method of promoting the growth of plants under salt stress conditions, which comprises administering an effective amount of a microalgae composition to the plant and/or plant-associated soil, such that the growth of the plant is increased at least 10% as compared to an untreated control under the salt stress condition. In some aspects the increase in growth of the treated plant (whether treated directly and/or growing in treated soil) is at least 15%, at least 20%, at least 25%, at least 30%, at least 35%, at least 40%, at least 45%, at least 50%, at least 55%, at least 60% or more such as about 65% increase in growth under the high salt conditions. In some aspects, the amount of excess salt in the salt stress condition is at least 25 mM additional NaCl, such as at least 35 mM, at least 50 mM, at least 60 mM, at least 70 mM, at least 75 mM, at least 80 mM, at least 90 mM, at least 100 mM, at least 110 mM, at least 120 mM, at least 125 mM, at least 135 mM, or at least 150 mM additional NaCl. In other aspects, the amount of salt has been determined to be at least 10%, at least about 15%, at least about 20%, at least about 25%, at least about 35%, at least about 40%, at least about 50%, at least about 66%, at least about 75%, at least about 90%, or even at least 100%, 150%, 200%, 250%, or 300% greater than either a desired growing condition, a historic soil condition, or both. In some aspects, the concentration of the microalgae composition that is administered to the plant and/or soil is in the range of 0.001%-0.25%, such as 0.001%-0.1%, such as 0.01%-0.1%, or such as 0.05%-0.1%. Typically the composition will comprise 0.1%-15% solids of the microalgae composition, such as 0.25-12.5%, 0.33-12%, 0.5-12%, 1-12%, 2-11%, 5-10%, or 7.5-12.5% microalgae solids; is formulated as a liquid composition; and is administered at a rate of 0.25-2.5 gal/acre, such as 0.33-2 gal/acre, or 0.5-1.75 gal/acre, for a period of 8-20 weeks, typically every 1-6 weeks, such as every 2-6 weeks, every 2-4 weeks, every 2 weeks, every 3 weeks, or every 4 weeks, for 1-10, 1-8, 1-6, 1-4, 2-10, 2-8, 2-6, 2-4, 3-10, 3-8, 3-6, 3-4, or 4-10, 4-8, 4-6, 6-10, or 6-8 applications, depending on the plant, soil type, etc. In one aspect, the microalgae comprises *Aurantiochytrium* material, such as post-extraction *Aurantiochytrium* material, examples of which are described elsewhere herein.

In another aspect, the invention provides a method for promoting the growth of roots of a plant comprising administering to the plant and/or plant-associated soil an effective amount of a microalgae composition of the invention, such that the number of roots, size of roots, total weight of roots, or a combination of any or all thereof is increased by at least about 20%, such as at least 30%, at least 40%, at least 50%, at least 75%, or even at least 100%. In some aspects, the method can result in an increase in root growth in any of these three dimensions by at least 150%>, at least 175%, at least 200%>, at least 250%, at least 300/o, at least 325%>, at least 350%, at least 375%, at least 400%, at least 425%, at least 450%, at least 475%, or even at least 500%. In some aspects, the amount of microalgae that is effective for increasing root concentration is in the concentration of 0.001%-0.25%, such as 0.001%-0.02%, 0.001%-0.01%, e.g., 0.0025%-0.009%, 0.0033%-0.009%, 0.004%-0.008%, or 0.005%-0.0075%. Typically, the composition will comprise 0.1%-15%> solids of the microalgae composition, such as 0.25-12.5%, 0.33-12%, 0.5-12%, 1-12%, 2-11%, 5-10%, or 7.5-12.5% microalgae solids; is formulated as a liquid composition; and is administered at a rate of 0.25-2.5 gal/acre, such as 0.33-2 gal/acre, or 0.5-1.75 gal/acre, for a period of 8-20 weeks, typically every 1-6 weeks, such as every 2-6 weeks, every 2-4 weeks, every 2 weeks, every 3 weeks, or every 4 weeks, for 1-10, 1-8, 1-6, 1-4, 2-10, 2-8, 2-6, 2-4, 3-10, 3-8, 3-6, 3-4, or 4-10, 4-8, 4-6, 6-10, or 6-8 applications, depending on the plant, soil type, etc. In some aspects the microalgae material comprises *Aurantiochytrium* material, such as post-extraction *Aurantiochytrium* material.

In another aspect, the invention provides methods for the prevention and/or reduction of one or more biotic stress(ors) and/or one or more plant diseas(es), such as, for example, white mold (*S. sclerotiorum*). An effective amount of a microalgae composition of the invention can be administered to the plant (directly and/or to the associated soil, but more typically such methods are performed by application to the plant) in an effective manner and effective amount, such as foliar administration of an effective amount of the microalgae composition in the case of white mold treatment or prevention. "Treatment" of the biotic stress/disease in this respect means reduction in the duration and/or extent of the incidence of the condition or disease. Compositions of the invention also or alternatively can be administered for the "prevention" of the disease/condition (reduction of the severity, as measured by, e.g., lessening of the duration, amount of deleterious impact (e.g., measured terms of frequency of occurrence of death, size reduction, etc.), and/or extent (as measured by amount of impacted area in the applicable plants) of the infection/disease). In one embodiment, an effective amount means a composition comprising the microalgae in a concentration of 0.001% to 0.01% (such as 0.005%-0.01%, 0.0075%-0.01%, 0.009-0.01%, 0.001%-0.008%, 0.001%-0.006%, 0.001%-0.005%, or 0.001%-0.003%). The amount of microalgae concentration, material, and route of administration is desirably effective to reduce S. sclerotiorum infection in a plant between about 15% to about 100%, such as at least about 20%, at least about 25%, at least about 30%, at least about 35%, at least about 40% or greater or 50% or greater, and in certain cases even 60% or greater or even 70% or greater (e.g., about 20%-100%, such as about 25% to about 95%, about 25% to about 90%, about 30% to about 80%, about 30% to about 75%, about 30% to about 70%, or about 35% to about 70%, such as about 40% to about 65%). Such reductions in infection can be measured with respect to a particular plant or as an average reduction in a population of plants. In one aspect, the microalgae composition comprises *Aurantiochytrium* material, such as post-extraction *Aurantiochytrium* material. In other particular aspects, the microalgae compositions of the invention are combined with one or additional products that treat, prevent, or otherwise modulate one or more diseases, such as white mold and/or white mold-associated conditions in the applicable plant(s) or plant population(s). In a particular aspect, the additional product is derived from macroalgae, such as kelp extract. In another aspect, the additional product also or alternatively is an anti-fungal product, such as an amount of vinclozolin, benomyl, and/or thiophanate methyl, in a concentration, administration amount, and administration protocol that alone or in combination with the microalgae composition to treat, prevent, or otherwise detectably, and desirably by at least 10%, at least 20%, at least 25%, or more, modulate white mold infection/disease in the applicable plant or plant population. In another aspect, the composition is also or alternatively administered in association with an agent that prevents rotting such as an ozone treatment. Associated administration in this context can mean co-administration or separate (serial) administration that is near enough in time to obtain the desired impact of administering the two or more agents in concert for the desired impact. The methods of the invention that are focused on the prevention of spread of disease such as white mold disease can advantageously be performed in areas that have been associated with recent infection, such as recent S. sclerotiorum infection, in areas that are associated with frequent infection as determined by longer term historical data or modeling, and/or in areas where S. sclerotiorum infection is predicted to occur through other means. Treatment methods can be performed where S. sclerotiorum is identified on plants or in a population of plants.

In another aspect, the invention provides a method of promoting the amount of active carbon in a soil, which comprises administering an effective amount of a microalgae composition of the invention to a soil such that the amount of active carbon in the soil is increased at least 5%, such as at least 10%, at least 12%, at least 15%, at least 17.5%, at least 20%, at least 22.5%, or at least 25%, within a period of 3 days, 5 days, 7 days, 10 days, 12 days, 14 days, 15 days, or 20 days. In one aspect, the microalgae comprises *Chlorella* material. In another aspect, the microalgae comprises *Aurantiochytrium* material. In another aspect, the invention comprises a combination of *Chlorella* material and *Aurantiochytrium* material. In another aspect, performance of the method results in achievement of an active carbon score of at least 65, at least 70, or at least 75, within a period of 5 days, 10 days, 15 days, or 20 days.

In still another facet, the invention provides a method for increasing the proportion of soil particles of 1-2 mm in size in a soil comprising administering an effective amount of a microalgae composition of the invention to a soil such that the amount of 1-2 mm particles present in the soil are increased by at least 20%, at least 25%, at least 30%, at least 35%, at least 40%, at least 50%, at least 60%, at least 65%, at least 70%, at least 75%, or more (such as about 80%), within a period of 10 days, 12 days, 14 days, or 15 days. In one aspect, the microalgae comprises *Aurantiochytrium* or *Chlorella*. In some aspects, the soil that receives the administration has been determined to have a lower proportion of 1-2 mm particles than is optimal for the growth of target plants, for the area and/or soil type that characterizes the soil before the treatment, or a combination thereof.

In still another dimension, the invention provides a method for increasing the amount of beneficial bacteria in a soil comprising administering an effective amount of a microalgae composition of the invention to a soil such that the amount of one or more beneficial bacterial species in the soil are increased by at least 25%, at least 35%, at least 50%>, at least 65%, at least 75%, at least 80%, at least 90%, or more. In some cases, the amount of beneficial bacteria in the soil are at least doubled by the application of the microalgae. In some aspects, the method comprises determining that the soil contains one or more endogenous, beneficial bacteria prior to application of the microalgae. The microalgae composition is typically applied 2-8 times, such as 3-6 times, such as 4-6 times, over a period of 4-30 weeks, such as 6-24 weeks, 8-24 weeks, 9-24 weeks, e.g., 8-16 weeks. The amount of microalgae applied is typically in the range of 0.1-3.5 gal/acre, for example 0.25 gal/acre-3 gal/acre, such as 0.33 gal/acre-2.5 gal/acre, such as 0.4-2.25 gal/acre, for example 0.5-1.5 gal acre, 0.5-1.25 gal/acre, or 0.5-1 gal/acre. In one aspect the beneficial bacteria comprises *Nitrospira* bacteria. In another aspect, the beneficial bacteria also or alternatively comprises *Gaiellales* bacteria. In still a further aspect, the beneficial bacteria also or alternatively comprises *Bacillus* bacteria. The bacteria can comprise another beneficial bacteria. A "beneficial bacteria" in this context means a bacteria that promotes the growth, quality, and/or health of one or more plant species.

EXAMPLES

Embodiments of the invention are exemplified and additional embodiments are disclosed in further detail in the following Examples, which are not in any way intended to limit the scope of any aspect of the invention described herein. The strain of microalgae identified as *Aurantiochytrium* sp. in some of the following examples was isolated from marine field samples (Mangrove, Fla.—Biscayne Bay) and sequenced for 18S. The sequences were compared with existing sequences on the National Center for Biotechnology Information (NCBI) GenBank database via Basic Local Alignment Search Tool (BLAST). The results of the sequence comparison showed strain' s sequence is positioned between two species of the genus *Aurantiochytrium* (*Schizochytrium*), with the closest BLAST hits having a 98.8% similarity to *Aurantiochytrium* (*Schizochytrium*) *limacinum* SR21 (accession number AB973564.1). Therefore, this isolated microalgae strain is referred to in the examples as *Aurantiochytrium* sp.

Example 1

A greenhouse experiment was performed to determine the effect of *Schizochytrium*- and *Chlorella*-based compositions on active carbon level and dry soil aggregate size distribution. Soil was collected from a fallow field previously planted with corn from Gilbert, Ariz. Soil was diluted by 40% with a peat based soil mix and perlite.

Quart pots were filled and drenched with *Schizochytrium*- or *Chlorella*-based compositions in concentrations ranging from 0.03-3% volume/volume in water. Water alone was included as the untreated control. Pots were kept moist by watering with water alone every 2 days. Soil samples were collected every 5 days for 2 weeks and assayed for active carbon and dry soil aggregate size distribution.

To obtain active carbon scores, soil samples were air dried and sieved to 2 mm. A 2.5 g sample of air-dried soil was placed in a 50-mL centrifuge tube filled with 20 mL of a 0.02 M potassium permanganate ($KMnO_4$) solution, which is deep purple in color. The soil and $KMnO_4$ were shaken for exactly 2 minutes to oxidize the active carbon in the sample. The purple color becomes lighter as a result of the oxidation reaction. The sample tube was then allowed to settle for 8 minutes, pipetted into a second tube, and diluted with distilled water. Absorbance was measured at 550 nm. The absorbance of a standard dilution series of the $KMnO_4$ was measured to create a calibration curve for interpreting the sample absorbance data. A formula was used to convert sample absorbance value to active carbon units of mg carbon per kg of soil (assay as published by Cornell University).

Dry soil aggregate size distribution was analyzed through use of a stacked sieve assay with each level of sieve containing a different sized mesh screen. A dry soil sample of approximately 50 g (exact weight obtained) was poured through a 4 mm sieve. Soil that passed through that sieve was then added to the top sieve pan in a set of 5 stacked pans, with each layer of the stack having progressively smaller screens and the bottom pan being a collection pan (5 layers: 2 mm sieve, 1 mm sieve, 0.5 mm sieve, 0.25 mm sieve, and catch pan). The stack of sieves was then shaken on an orbital shaker for 5 minutes. Larger aggregates were caught in the higher sieves with only dust passing through to the bottom catch pan. The amount of material caught on each sieve level was then weighed and a simple calculation used to determine the percent of total soil content, represented by each aggregate size.

Figure 4:
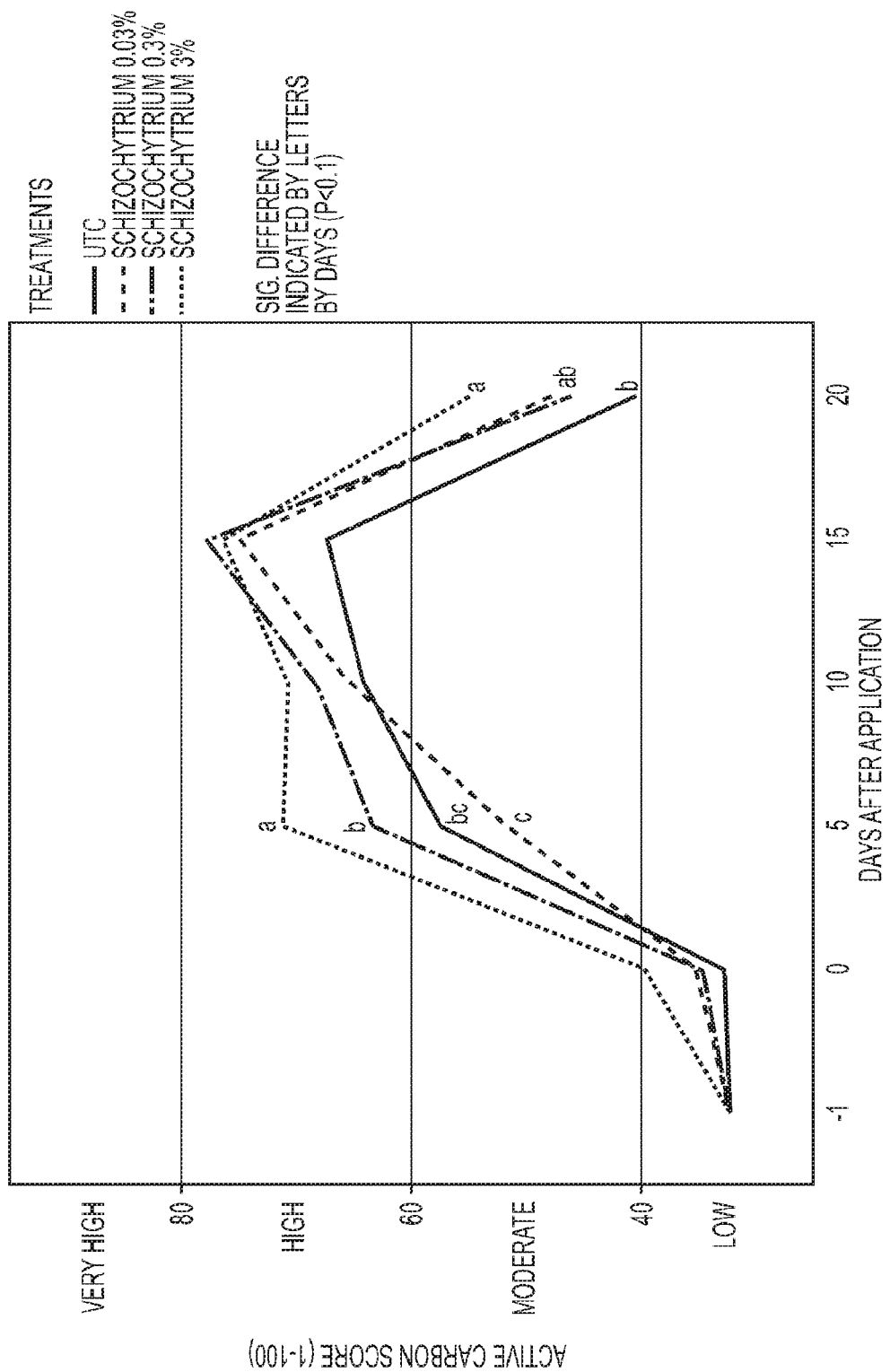
FIG. 4 depicts results of an experiment analyzing the effect of *Schizochytrium* compositions on soil active carbon score.
Figure 5:
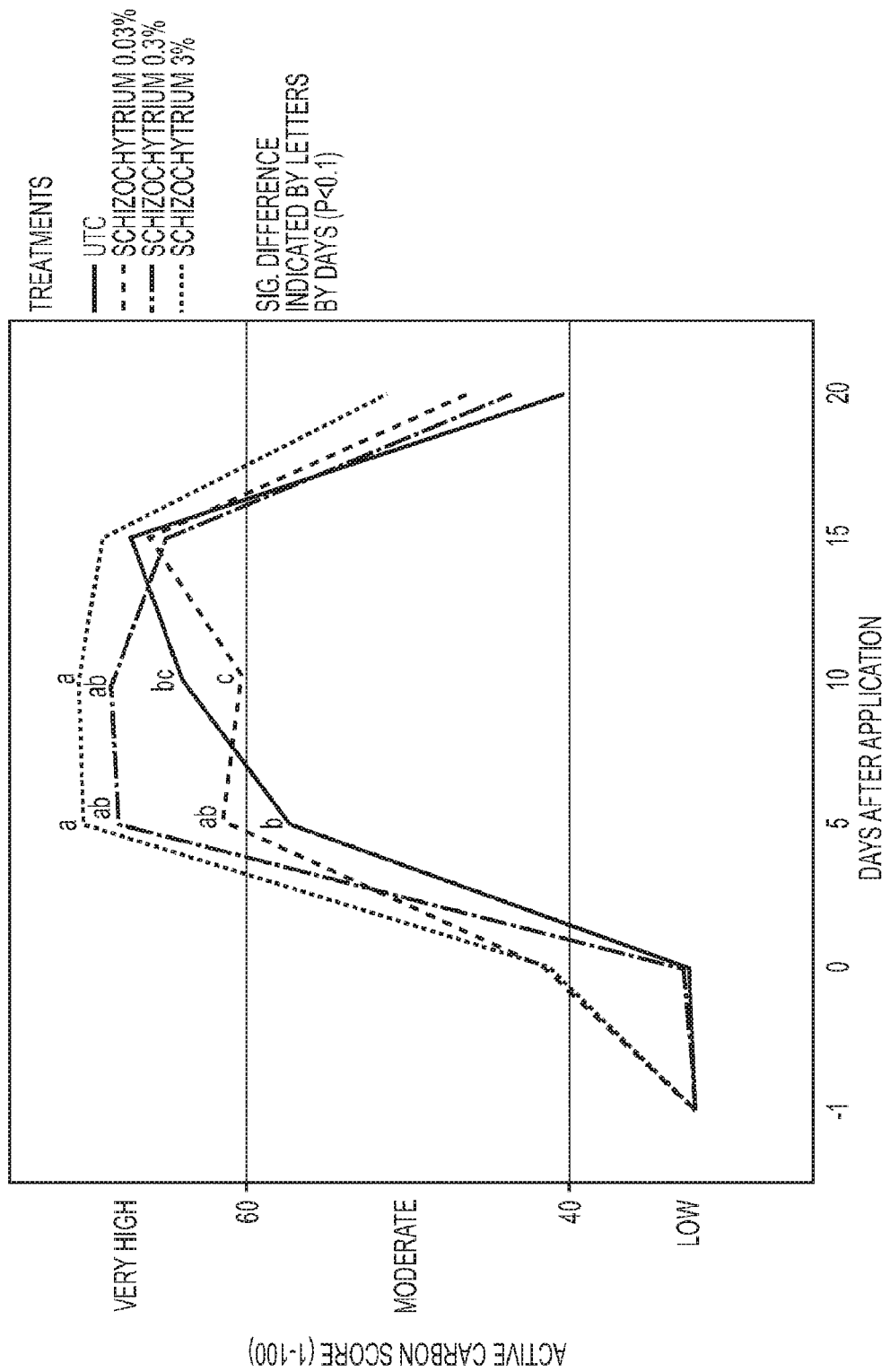
FIG. 5 depicts results of an experiment analyzing the effect of *Schizochytrium* compositions on soil active carbon score.
Figure 6:
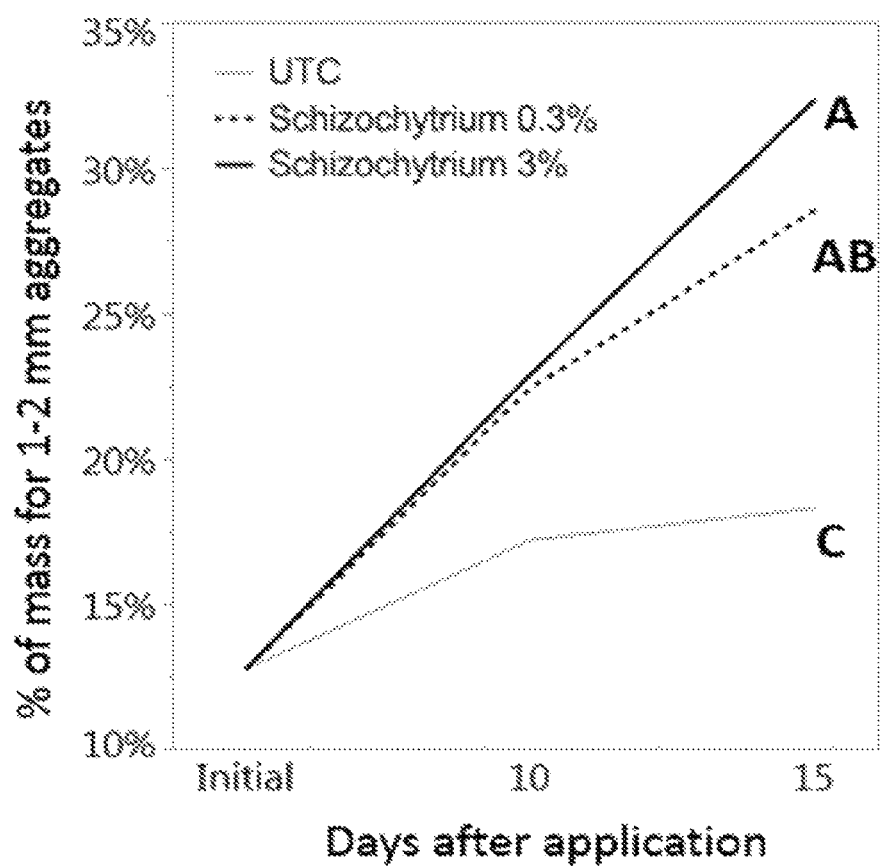
FIG. 6 depicts results of an experiment analyzing the effects of *Schizochytrium* compositions on soil aggregation.
Figure 7:
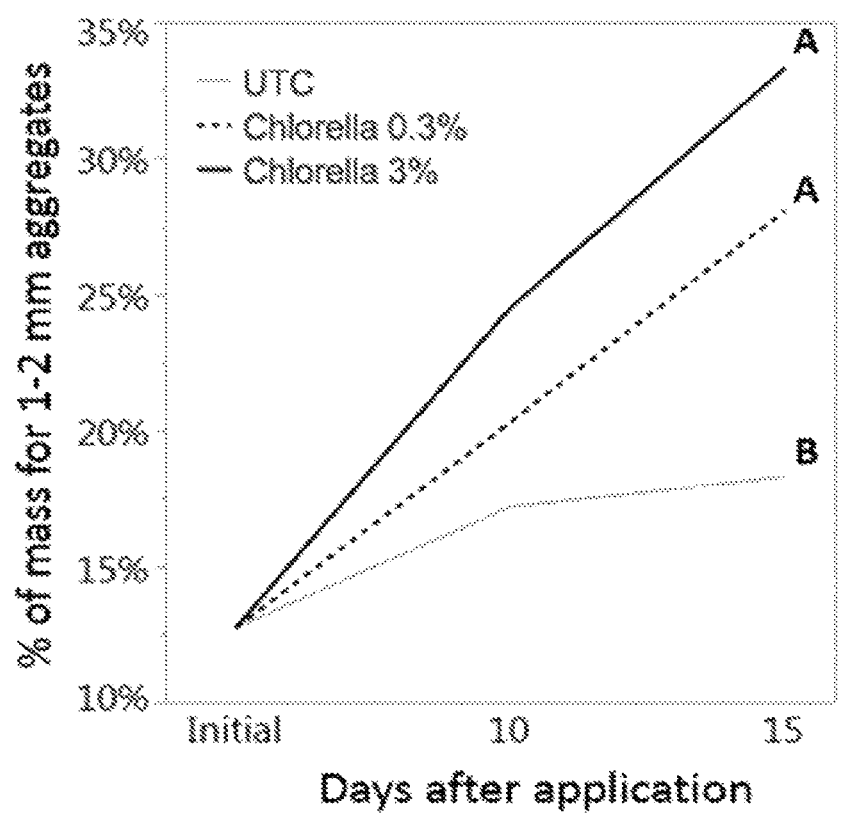
FIG. 7 depicts results of an experiment analyzing the effects of *Chlorella* on soil aggregation.

Results of active carbon assays for *Schizochytrium*-based compositions are shown in FIGS. 4 and 5 and Table 1. Results of active carbon assays for *Chlorella*-based compositions are shown in Table 1. Results of dry soil aggregate size distribution for *Schizochytrium*-based compositions are shown in FIG. 6 and Table 2. Results of dry soil aggregate size distribution for *Chlorella*-based compositions are shown in FIG. 7 and Table 2.

TABLE 1

| | Active Carbon Score | | | | | |
|---|---|---|---|---|---|---|
| Treatment | Initial Sample (−1 days) | Immediately after application (0 days) | Day 5 | Day 10 | Day 15 | Day 20 |
| Schizochytrium, 3% | 32 | 39 | 73 | 71 | 76 | 56 |
| Schizochytrium, 0.3% | 32 | 35 | 64 | 68 | 77 | 47 |
| Schizochytrium, 0.03% | 32 | 35 | 52 | 65 | 74 | 48 |
| Chlorella, 3% | 32 | 42 | 70 | 70.5 | 69 | 52 |
| Chlorella, 0.3% | 32 | 33 | 68 | 68.5 | 65 | 44 |
| Chlorella, 0.03% | 32 | 41 | 62 | 61 | 66 | 47 |
| UTC | 32 | 33 | 57 | 64 | 66 | 40 |

TABLE 2

| | % of Mass for 1-2 mm Aggregates | | |
|---|---|---|---|
| Treatment | Initial | Day 10 | Day 15 |
| Schizochytrium, 3% | 13 | 23 | 32.5 |
| Schizochytrium, 0.3% | 13 | 22.5 | 28 |
| Chlorella, 3% | 13 | 24 | 33 |
| Chlorella, 0.3% | 13 | 20 | 28 |
| UTC | 13 | 17 | 18 |

As shown in FIGS. 4, 5, and Table 1, the *Schizochytrium*- and *Chlorella*-based compositions with the highest concentrations of 3% demonstrated a statistically significant increase in active carbon over untreated control. After a single application of both the *Schizochytrium*- and *Chlorella*-based compositions, active carbon in the soil increased from a score falling in the 'low' health range to the 'high' health range. The 'high' range score was maintained by both microalgae compositions at the highest concentration (3%) for approximately 10 days. The rate of increase in active carbon followed a dose-dependent pattern, with the compositions at 3% showing the fastest score increases, followed by the 0.3% composition and finally by the 0.03% composition. While water alone also increased the active carbon level over time, it did not do so as quickly as the algae compositions at 0.3% and 3% concentrations, nor did it reach the same peak active carbon score of any of the *Schizochytrium*-based compositions. In addition, water alone failed to maintain an active carbon score in the 'high' range for as long as either the 3% or 0.3% *Schizochytrium*-based compositions and was outperformed by all *Chlorella*-based compositions in this regard.

As shown in FIGS. 6, 7 and Table 2, both *Schizochytrium*- and *Chlorella*-based compositions at both 0.3% and 3% demonstrated statistically significant increases in the percent (by mass) of the desirable dry soil aggregate size 1-2 mm over untreated control. The percent mass of dry soil aggregates of 1-2 mm increased for 15 days after algae-based compositions were applied. The algae-based compositions at a concentration of 3% more than doubled the percent mass of dry soil aggregates of 1-2 mm over the course of the 15-day study.

Example 2

Field trial experiments were conducted on sweet corn, snap peas, and snap beans to evaluate the effects of *Schizochytrium*- and *Chlorella*-based compositions on soil microbial communities.

Sweet corn, snap beans, and snap peas were transplanted in adjacent fields in Paynesville, Minn. All plots were managed according to grower standard practice (see Table 3). Soil from treated and untreated plots was collected from the root zone of each plot during harvest and evaluated for bacterial community changes and bacterial community structure using next-generation Illumina MiSeg™ sequencing. Sequences were analyzed using the QIHvIE-2 software package; DADA2 pipeline for sequence variant annotation. Beta-diversity using PERMANOVA of unweighted unifrac distances. Differential abundance of sequence variants using the QIIJVIE-1 implementation of the DESeq2 algorithm as well as the QIIJ\tIE-1 "group-significance.py" script. Sequence variants showing significant differential abundance were analyzed for further phylogenetic placement with a bootstrapped neighbor joining tree of curated 16S sequences and an outgroup of *Aquifex aeolicus*.

TABLE 3

STUDY PARAMETERS

| Crop & variety | Sweet corn, Temptation | Snap bean, Provider | Snap pea, Sugar Sprint |
|---|---|---|---|
| Location | Crow River Research Farm, Paynesville MN | | |
| Transplanting date | Jun. 24, 2016 | Jun. 25, 2016 | Jun. 23, 2016 |
| Harvest dates | Sep. 11, 2016 | Sep. 8, 2016 | Aug. 25, 2016 |
| Planting density | 34,800 plants/A | 8,800 plants/A | 8,600 plants/A |
| Irrigation | Via pivot as needed | | |
| Fertilizer at planting | 120 lbs/A Urea | | 80 lbs/A Urea |
| | 30 lbs/AK, 30 lbs/AP, lib/A Zn, lib/AB | | |
| Soil type | Estherville sandy loam, silt loam | | |
| Plot size | 5' W × 20' L | | |
| Replication | 8 plots per treatment, RCB design | | |
| Product applied via temporary drip at planting: | then every 2 wks (6 total) | | then every 2 wks (5 total) |

Figure 8:
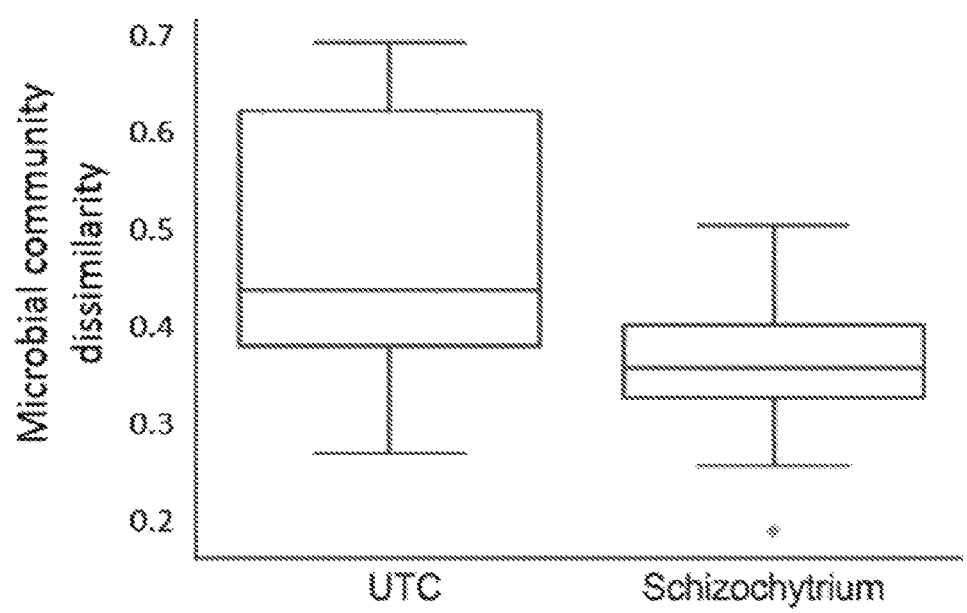
FIG. 8 depicts the results of an experiment analyzing the effects of *Schizochytrium* compositions on soil microbial communities.
Figure 9:
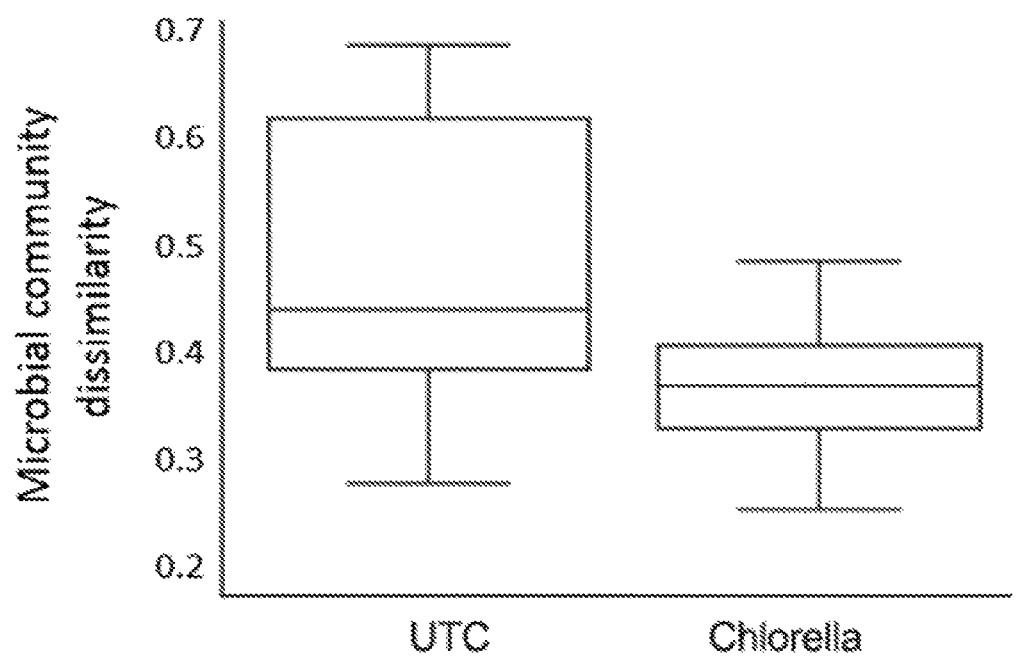
FIG. 9 depicts the results of an experiment analyzing the effects of *Chlorella* compositions on soil microbial communities.
Figure 10:
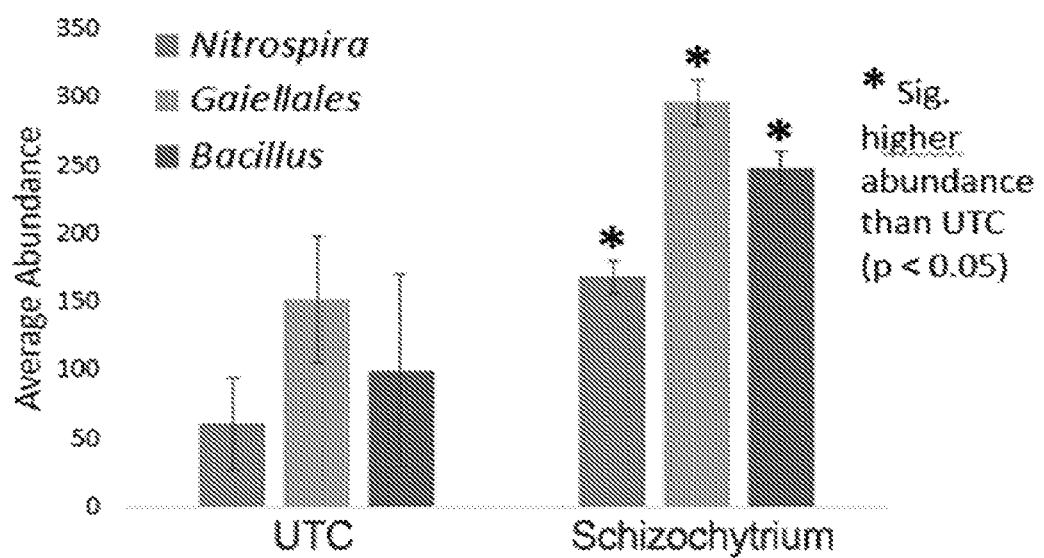
FIG. 10 depicts the results of an experiment analyzing the effects of *Schizochytrium* compositions on the beneficial soil bacteria *Nitrospira, Gaiellales*, and *Bacillus*.
Figure 11:
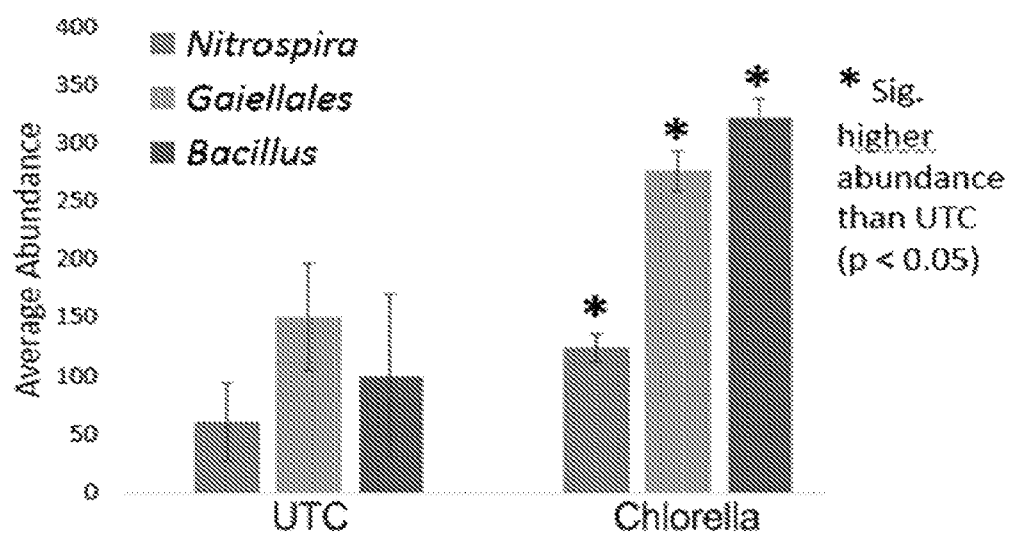
FIG. 11 depicts the results of an experiment analyzing the effects of *Chlorella* compositions on the beneficial soil bacteria *Nitrospira, Gaiellales*, and *Bacillus*.

Results of soil community similarity analysis are shown as dissimilarity plots in FIGS. 8 and 9. Results from the analysis of levels of beneficial soil bacteria are shown in FIGS. 10 and 11.

It will be apparent to one skilled in the art that various substitutions and modifications can be made to the invention disclosed herein without departing from the scope and spirit of the invention.

Those skilled in the art recognize that the aspects and embodiments of the invention set forth herein can be practiced separate from each other or in conjunction with each other. Therefore, combinations of separate embodiments are within the scope of the invention as disclosed herein.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of increasing aggregation in a soil comprising the step of administering to the soil an amount of a pasteurized microalgae material to increase aggregation in the soil compared to a substantially identical untreated soil, wherein the microalgae material comprises *Schizochytrium* cells.

2. The method of claim 1, wherein administering the microalgae material increases the percentage of soil mass present as 1-2 mm aggregates.

3. The method of claim 1, wherein the amount of microalgae material is effective to increase the soil aggregation over a period of 15 days.

4. The method of claim 1, wherein the microalgae material is provided as a liquid formulation composition comprising 0.1-15% solids from one or more cultures of the microalgae.

5. The method of claim 1, wherein the microalgae material comprises whole cells, lysed cells, or a combination thereof.

6. The method of claim 1, wherein microalgae material comprises excreted products.

7. The method of claim 6, wherein the excreted products are excreted polysaccharides (EPS).

8. The method of claim 1, wherein a single application of microalgae material is made to the soil.

9. The method of claim 1, wherein multiple applications of microalgae material are made to the soil.

10. The method of claim 1, wherein the microalgae material is administered to soil associated with a plant.

11. The method of claim 1, wherein the microalgae material is administered by irrigation into the soil in-furrow, via drip irrigation, and/or with a broadcast application.

12. A method of enhancing the active carbon score of a soil, comprising administering an amount of a pasteurized microalgae material to the soil to increase the active carbon score of the soil compared to a substantially identical untreated soil, wherein the microalgae material comprises *Schizochytrium* cells.

13. The method of claim 12, wherein the microalgae material is provided as a liquid formulation composition comprising 0.1-15% solids from one or more cultures of the microalgae.

14. The method of claim 12, wherein the microalgae material comprises whole cells, lysed cells, or a combination thereof.

15. The method of claim 12, wherein microalgae material comprises excreted products.

16. The method of claim 15, wherein the excreted products are excreted polysaccharides (EPS).

17. The method of claim 12, wherein a single application of microalgae material is made to the soil.

18. The method of claim 12, wherein multiple applications of microalgae material are made to the soil.

19. The method of claim 12, wherein the microalgae material is administered to soil associated with a plant.

20. The method of claim 12, wherein the microalgae material is administered by irrigation into the soil in-furrow, via drip irrigation, and/or with a broadcast application.

* * * * *